US005705334A

United States Patent [19]
Lippard et al.

[11] Patent Number: 5,705,334
[45] Date of Patent: Jan. 6, 1998

[54] USES FOR DNA STRUCTURE-SPECIFIC RECOGNITION PROTEIN

[75] Inventors: Stephen J. Lippard, Cambridge; John M. Essigmann, Brookline, both of Mass.; Brian Donahue, Menlo Park, Calif.; Jeffrey H. Toney, Westfield, N.J.; Suzanne L. Bruhn, Cambridge, Mass.; Pieter M. Pil, New Haven, Conn.; Steven J. Brown, La Jolla, Calif.; Patti J. Kellett, Cincinnati, Ohio

[73] Assignee: Massachusetts Institute of Technology, Cambridge, Mass.

[21] Appl. No.: 328,809

[22] Filed: Oct. 25, 1994

Related U.S. Application Data

[60] Continuation-in-part of Ser. No. 258,442, Jun. 9, 1994, which is a division of Ser. No. 814,964, Dec. 26, 1991, Pat. No. 5,359,047, which is a continuation-in-part of Ser. No. 539,906, Jun. 18, 1990, abandoned, which is a continuation-in-part of Ser. No. 410,981, Sep. 22, 1989, abandoned, which is a continuation-in-part of Ser. No. 247,774, Sep. 22, 1988, abandoned.

[51] Int. Cl.$^6$ .................................................. C12N 15/00
[52] U.S. Cl. .................................................. 435/6; 436/7.1
[58] Field of Search ....................... 435/6, 7.1; 436/503; 424/617, 649

[56] References Cited

U.S. PATENT DOCUMENTS 5,359,047  10/1994  Donahue et al. ................. 536/23.5

FOREIGN PATENT DOCUMENTS

| 0057553 | 8/1982 | European Pat. Off. . |
|---|---|---|
| WO 90/03396 | 4/1990 | WIPO . |
| WO 95/27784 | 10/1995 | WIPO . |
| WO 95/28948 | 11/1995 | WIPO . |

OTHER PUBLICATIONS

Takahara et al., "Crystal Structure of Double-Stranded DNA Containing the Major Adduct of the Anticancer Drug Cisplatin", *Nature*, 377:649–652 (Oct. 19, 1995).

Ingrid Wickelgren, "Protein Sculptors That Help Turn On Genes", *Science*, 270:1587–1588 (Dec. 8, 1995).

Billings et al. (1994) "Proteins binding to cisplatin-damaged DNA in human cell lines", 12 (6) *Cancer Invest.*, 597–604.

Chao (1994) "Decreased accumulation as a mechanism of resistance to cis-diamminedichloroplatinum (II) in cervix carcinoma Hela cells", 45 (0) *Mol. Pharmacol.*, 1137–1144.

Chao et al. (1994) "Use of a monoclonal-antibody to detect DNA-damage caused by the anticancer drug cis-diamminedichloroplatinum (II) in-vivo and in-vitro", 354 (1) *FEBS Lett.*, 103–109.

Dabholkar et al. (1994) "Messenger RNA levels of XPAC and ERCC1 in ovarian cancer tissue correlate with response to platinum-based chemotherapy", 94 (2) *J. Clin. Invest.*, 703–708.

Lippard (1994), "Structural and Biological Consequences of Platinum Anticancer Drug Binding to DNA," Chapter 4 of *Proceedings of the Robert A. Welch Foundation 37th Conference on Chemical Research, 40 Years of the DNA Double Helix*, Oct. 25–26, 1993, The Westin Oaks Hotel, Houston, Texas.

Marples et al. (1994) "Recognition of Platinum-Induced DNA—damage by nuclear proteins—screening for mechanisms", 9 (5) *Anti-Cancer Drug Design*, 389–399.

Murphy et al. (1994) "Altered levels of DNA—damage recognition proteins in MCF-7 breast carcinoma cells resistant to adriamycin" 35 (0) *Proc. Am. Assoc. Cancer Res. Ann. Mtgs.* 466, Presented at 85th Ann. Mtg. Am. Assoc. Cancer Res., San Francisco California, USA, Apr. 10–13, 1994.

Putnam et al. (1994) "The RNA polymerase transactivator upstream binding factor reqires its dimerization domain and high-mobility-group (HMG) box 1 to bends, wrap, and positively supercoil enhancer DNA", 14 (10) *Mol. Cell. Bio.*, 6476–6488.

Sanda et al. (1994) "Demonstration of a rational strategy for human prostate cancer gene therapy", 151 *The Journal of Urology*, 622–628.

Wolffe, Alan P. (1994), "Architectural Transcription Factors", 264 *Science*, 1100–1101.

Bradley et al. (1993), "Mutagenicity and Genotoxicity of the Major DNA Adduct of the Anti-Tumor Drug cis-Diamminedichloroplatinum (II), " 32 *Biochem.*, 982–988.

Brown et al. (1993), "Ixr1, a Yeast Protein That Binds to Platinated DNA and Confers Sensitivity to Cisplatin," 261 *Science* 603–605.

Bruhn et al. (1993), "Isolation and Characterization of cDNA Clones Encoding the Drosophila Homolog of the HMG-Box SSRP Family That Recognizes Specific DNA Structures," 21 *Nucl. Acids Res.*, 1643–1646.

King et al. (1993), "The SRY High-Mobility-Group Box Recognizes DNA by Partial Intercalation in the Minor Groove: A Topological Mechanism of Sequence Specificity," 90 *Proc. Natl. Acad. Sci. U.S.A.*, 11990–11994.

Mulligan, Richard C. (1993) "The Basic Science of Gene Therapy", 260 *Science*, 926–932.

Pil et al. (1993), "High-Mobility Group 1 Protein Mediates DNA Bending as Determined by Ring Closures," 90 *Proc. Natl. Acad. Sci. U.S.A.*, 9465–9469.

(List continued on next page.)

*Primary Examiner*—Marianne P. Allen
*Attorney, Agent, or Firm*—Testa, Hurwitz & Thibeault, LLP

[57] ABSTRACT

Methods disclosed herein capitalize on the ability of DNA Structure Specific Recognition Proteins (SSRPs) to bind to genomic lesions formed by chemotherapeutic agents, particularly cisplatin-type agents. Methods are provided for predicting whether an agent that damages DNA will also be cytotoxic, and for predicting whether particular eukaryotic cells will be susceptible to killing by a genotoxic drug. A screening method is provided for identifying new genotoxic drugs that produce SSRP-recognized lesions in DNA. Methods also are provided for sensitizing particular eukaryotic cells to killing by chemotherapeutic agents, particularly cisplatin-type drugs.

13 Claims, 5 Drawing Sheets

OTHER PUBLICATIONS

Sanda et al. (1993), "The Retroviral Vector MFG Allows High Efficiency Transduction of Human Prostate Cancer Cells: Implications for Gene Therapy of Prostate Cancer", March, *J. of Cell Biochemistry*, Suppl. 17D, p. 120, Abstract NZ 409.

Weir et al. (1993), "Structure of the HMG Box Motif in the B–Domain of HMG1," 12 (4) *EMBO J.* 1311–1319.

Baum, Rudy (1992), "Protein Found That Binds to Cisplatin–DNA Adducts", Apr. 20, *C & EN.*, 19–20.

Bianchi et al. (1992), "The DNA Binding Site of HMG 1 Protein is Composed of Two Similar Segments (HMG Boxes), Both of Which Have Counterparts in Other Eukaryotic Regulatory Proteins," 11 (3) *EMBO J.*, 1055–1063.

Bruhn et al. (1992), "Isolation and Characterization of Human cDNA Clones Encoding a High Mobility Group Box Protein That Recognizes Structural Distortions to DNA Caused by Binding of the Anticancer Agent Cisplatin", 89 *Proc. Natl. Acad. Sci. U.S.A.*, 2307–2311.

Culver et al. (1992) "In Vivo Gene Transfer with Retroviral Vector–Producer Cells for Treatment of Experimental Brain Tumors", 256 *Science*, 1550–1552.

Dabholkar et al. (1992), "Determinants of Cisplatin Sensitivity in Non–Malignant Non–Drug Selected Human T Cells," 274 *Mut. Res.*, 45–56.

Ferrari et al. (1992), "SRY, Like HMG 1, Recognizes Sharp Angles in DNA," 11 (12) *EMBO J.*, 4497–4506.

Giese et al. (1992), "The HMG Domain of Lymhoid Enhancer Factor 1 Bends DNA and Facilitate Assembly of Functional Nucleoprotein Structures," 69 *Cell*, 185–195.

Hughes et al. (1992), "Purification of Nuclear Proteins That Bind to Cisplatin–Damaged DNA," 267 *J. Biol. Chem.*, 13520–13527.

Jantzen et al. (1992), "Multiple Domains of the RNA Polymerase I Activator hUBF Interact With the TATA–Binding Protein Complex hSL1 to Mediate Transcription," 6 *Genes & Dev.* 1950–1963.

Lilley (1992), "HMG Has DNA Wrapped Up," 357 *Nature*, 282–283.

Pil et al. (1992), "Specific Binding of Chromosomal Protein HMG 1 to DNA Damaged by the Anticancer Drug Cisplatin," 256 *Science*, 234–237.

Podda et al. (1992) "Transfer and expression of the human multiple drug resistance gene into live mice", 89 *Proc. Natl. Acad. Sci. USA*, 9676–9680.

Putnam et al. (1992), "Cooperative Binding of the Xenopus RNA Polymerase I Transcription Factor xUBF to Repetitive Ribosomal Gene Enhancers," 12 (11) *Mol & Cell. Biol.*, 4970–4980.

Sorrentino et al. (1992), "Selection of Drug–Resistance Bone Marrow Cells in Vivo After Retroviral Transfer of Human MDR1", 257 *Science*, 99–103.

Szymkowski et al. (1992), "An Intrastrand d(GpG) Platinum Crosslink in Duplex M13 DNA is Refractory to Repair by Human Cell Extracts," 89 *P.N.A.S. USA* 10772–10776.

Zhen et al. (1992), "Increased Gene–Specific Repair of Cisplatin Interstrand Cross–Links in Cisplatin–Resistant Human Ovarian Cancer Cell Lines," 12 (9) *Mol. and Cell. Biol.*, 3689–3698.

Andrews et al. (1991), "Characterization of Binding Proteins from Ovarian Carcinoma and Kidney Tubule Cells that are Specific for Cisplatin Modified DNA", 3 *Cancer Comm.*, 1–10.

Chao et al. (1991) "Identification of inducible damage–recognition proteins that are overexpressed in HeLa cells resistant to cisdiammine–dichloroplatinum (II)", 277 *Biochem. J.*, 875–878.

Diffley et al. (1991), "A close relative of the nuclear, chromosomal high–mobility group protein HMG1 in yeast mitochondria", 88 *Proc. Natl. Aca. Sci. USA*, 7864–7868.

Donahue et al. (1991), "A Protein from Mammalian Cells that Recognizes Platinated DNA", *Platinum and Other Metal Coord. Compounds in Cancer Chemotherapy*, 241–251 (S.B. Howell, ed.; Plenum Press NY).

Giese et al. (1991), "DNA–binding properties of the HMG domain of the lymphoid–specific transcriptional regulator LE–1", 5 *Genes & Devel.*, 2567–2578.

Jones et al. (1991), "Gene–specific Formation and Repair of Cisplatin Intrastrand Adducts and Interstrand Cross–links in Chinese Hamster Ovary Cells," 266 *J. Bio. Chem.*, 7101–7107.

Shirakata et al. (1991), "HMG1–Related DNA–Binding Protein Isolated with V–(D)–J Recombination Signal Probes," 11 *Mol. Cell. Biol.*, 4528–4536.

Bruhn et al. (1990), "Biological Processing of DNA Modified by Platinum Compounds," 38 *Prog. Inorg. Chem. Bioinorg. Chem.*, 477–516.

Bustin et al. (1990), "Structural Features of the HMG Chromosomal Proteins and Their Genes," 1049 *Biochem. & Biophys. Acta*, 231–243.

Donahue et al. (1990), "Characterization of a DNA Damage–Recognition Protein from Mammalian Cells that Binds Specifically to Intrastrand d(GpG) DNA Adducts of the Anticancer Drug Cisplatin," 29 *Biochemistry*, 5872–5880.

Hodge et al. (1990), "Upstream Activation and Repression Elements Control Transcription of the Yeast COX5b Gene", 10 (10) *Mol. & Cell. Biol.*, 5511–5520.

Jantzen et al. (1990), "Nuclear transcription factor hUBF contains a DNA–binding motif with homology to HMG proteins," 344 *Nature*, 830–736.

Lenz et al. (1990), "Identification of a mammalian nuclear factor and cDNA–encoded proteins that recognize DNA containing apurinic sites," 87 *Proc. Natl. Acad. Sci. USA*, 3396–3400.

Short et al. (1990) "Gene Delivery to Glioma Cells in Rat Brain by Grafting of a Retrovirus Packaging Cell Line", 27 *J. Neur. Res.*, 427–439.

Sorenson et al. (1990), "Analysis of Events Associated with Cell Cycle Arrest at $G_2$ Phase and Cell Death Induced by Cisplatin," 82 *J. Natl. Cancer Inst.*, 749–755.

Batist et al. (1989), "Enhanced DNA Cross–Link Removal: The Apparent Mechanism of Resistance in a Clinically Relevant Melphalan–Resistant Human Breast Cancer Cell Line," 36 *Mol. Pharmacol.* 224–230.

Toney et al. (1989), "Isolation of cDNAs encoding a human protein that binds selectively to DNA modified by the anticancer drug cisdiammine–dichloroplatinum (II)," 86 *Proc. Natl. Acad. Sci. USA* 8328–8332.

Wen et al. (1989) "A human placental cDNA clone that encodes non–histone chromosomal protein HMG–1," 17 *Nucl. Acids Res.* 1197–1215.

Bell et al. (1988), "Functional Cooperativity Between Transcription Factors UBF1 and SL1 Mediates Human Ribosomal RNA Synthesis," 241 *Science* 1192–1197.

Rice et al. (1988), "The major adduct of the antitumor drug cis–diamminedichloroplatinum (II) with DNA bends the duplex by ~40° toward the major groove," 85 *Proc. Natl. Acad. Sci. USA* 4158–4161.

Fichtinger–Schepman et al. (1987), "cis–Diamminedichloroplatinum(II)–induced DNA Adducts in Peripheral Leukocytes from Seven Cancer Patients: Quantitative Immunochemical Detection of the Adduct Induction and Removal after a Single Does of cis–Diamminodichloroplatinum(II)," 47 *Cancer Res.* 3000–3004.

Lee et al. (1987), "Characterization of cDNA sequences corresponding to three distinct HMG–1 mRNA species in line CHO Chinese hamster cells and cell cycle expression of the HMG–1 gene," 15 *Nucl. Acids Res.* 5051–5068.

Paonessa et al. (1987), "Nucleotide sequence of rat liver HMG1 cDNA," 15 *Nucl. Acids Res.* 9077.

Jones et al. (1985) "Cis–Diamminedichloroplatinum(II)–Induced Acute Renal Failure in the Rat," 52 *Lab. Invest.* 363–374.

Cone et al. (1984) "High–efficiency gene transfer into mammalian cells: Generation of helper–free recombinant retrovirus with broad mammalian host range", 81 *Proc. Natl. Acad. Sci. USA,* 6349–6353.

Loehrer, et al. (1984) "Diagnosis and Treatment of Drugs Five Years Later—Cisplatin," 100 *Ann. Int. Med.* 704–713.

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
       ( A ) LENGTH: 2839 base pairs
       ( B ) TYPE: nucleic acid
       ( C ) STRANDEDNESS: double
       ( D ) TOPOLOGY: linear ( i i ) MOLECULE TYPE: cDNA ( v i ) ORIGINAL SOURCE:
       ( A ) ORGANISM: Homo sapiens ( v i i ) IMMEDIATE SOURCE:
       ( B ) CLONE: human SSRP - composite of six overlapping cDNA clones ( v i i i ) POSITION IN GENOME:
       ( A ) CHROMOSOME/SEGMENT: 11q12

( i x ) FEATURE:
       ( A ) NAME/KEY: CDS
       ( B ) LOCATION: 275..2404

( x i ) SEQUENCE DESCRIPTION: SEQ ID NO:1:

```
GAATTCCGTA  CGGCTTCCGG  TGGCGGGACG  CGGGGCCGCG  CACGCGGGAA  AAGCTTCCCC      60
GGTGTCCCCC  CATCCCCCTC  CCCGCGCCCC  CCCCGCGTCC  CCCCAGCGCG  CCCACCTCTC     120
GCGCCGGGGC  CCTCGCGAGG  CCGCAGCCTG  AGGAGATTCC  CAACCTGCTG  AGCATCCGCA     180
```

-continued

| | |
|---|---|
| CACCCACTCA GGAGTTGGGG CCCAGCTCCC AGTTTACTTG GTTTCCCTTG TGCAGCCTGG | 240 |
| GGCTCTGCCC AGGCCACCAC AGGCAGGGGT CGAC ATG GCA GAG ACA CTG GAG<br>                                                                       Met Ala Glu Thr Leu Glu<br>                                                                         1                                  5 | 292 |
| TTC AAC GAC GTC TAT CAG GAG GTG AAA GGT TCC ATG AAT GAT GGT CGA<br>Phe Asn Asp Val Tyr Gln Glu Val Lys Gly Ser Met Asn Asp Gly Arg<br>                    10                            15                            20 | 340 |
| CTG AGG TTG AGC CGT CAG GGC ATC ATC TTC AAG AAT AGC AAG ACA GGC<br>Leu Arg Leu Ser Arg Gln Gly Ile Ile Phe Lys Asn Ser Lys Thr Gly<br>            25                            30                            35 | 388 |
| AAA GTG GAC AAC ATC CAG GCT GGG GAG TTA ACA GAA GGT ATC TGG CGC<br>Lys Val Asp Asn Ile Gln Ala Gly Glu Leu Thr Glu Gly Ile Trp Arg<br>      40                          45                            50 | 436 |
| CGT GTT GCT CTG GGC CAT GGA CTT AAA CTG CTT ACA AAG AAT GGC CAT<br>Arg Val Ala Leu Gly His Gly Leu Lys Leu Leu Thr Lys Asn Gly His<br>55                            60                            65                            70 | 484 |
| GTC TAC AAG TAT GAT GGC TTC CGA GAA TCG GAG TTT GAG AAA CTC TCT<br>Val Tyr Lys Tyr Asp Gly Phe Arg Glu Ser Glu Phe Glu Lys Leu Ser<br>                    75                            80                            85 | 532 |
| GAT TTC TTC AAA ACT CAC TAT CGC CTT GAG CTA ATG GAG AAG GAC CTT<br>Asp Phe Phe Lys Thr His Tyr Arg Leu Glu Leu Met Glu Lys Asp Leu<br>            90                            95                            100 | 580 |
| TGT GTG AAG GGC TGG AAC TGG GGG ACA GTG AAA TTT GGT GGG CAG CTG<br>Cys Val Lys Gly Trp Asn Trp Gly Thr Val Lys Phe Gly Gly Gln Leu<br>          105                          110                          115 | 628 |
| CTT TCC TTT GAC ATT GGT GAC CAG CCA GTC TTT GAG ATA CCC CTC AGC<br>Leu Ser Phe Asp Ile Gly Asp Gln Pro Val Phe Glu Ile Pro Leu Ser<br>          120                          125                          130 | 676 |
| AAT GTG TCC CAG TGC ACC ACA GGC AAG AAT GAG GTG ACA CTG GAA TTC<br>Asn Val Ser Gln Cys Thr Thr Gly Lys Asn Glu Val Thr Leu Glu Phe<br>135                            140                            145                            150 | 724 |
| CAC CAA AAC GAT GAC GCA GAG GTG TCT CTC ATG GAG GTG CGC TTC TAC<br>His Gln Asn Asp Asp Ala Glu Val Ser Leu Met Glu Val Arg Phe Tyr<br>                    155                            160                          165 | 772 |
| GTC CCA CCC ACC CAG GAG GAT GGT GTG GAC CCT GTT GAG GCC TTT GCC<br>Val Pro Pro Thr Gln Glu Asp Gly Val Asp Pro Val Glu Ala Phe Ala<br>          170                          175                          180 | 820 |
| CAG AAT GTG TTG TCA AAG GCG GAT GTA ATC CAG GCC ACG GGA GAT GCC<br>Gln Asn Val Leu Ser Lys Ala Asp Val Ile Gln Ala Thr Gly Asp Ala<br>                185                          190                        195 | 868 |
| ATC TGC ATC TTC CGG GAG CTG CAG TGT CTG ACT CCT CGT GGT CGT TAT<br>Ile Cys Ile Phe Arg Glu Leu Gln Cys Leu Thr Pro Arg Gly Arg Tyr<br>200                            205                            210 | 916 |
| GAC ATT CGG ATC TAC CCC ACC TTT CTG CAC CTG CAT GGC AAG ACC TTT<br>Asp Ile Arg Ile Tyr Pro Thr Phe Leu His Leu His Gly Lys Thr Phe<br>215                            220                            225                            230 | 964 |
| GAC TAC AAG ATC CCC TAC ACC ACA GTA CTG CGT CTG TTT TTG TTA CCC<br>Asp Tyr Lys Ile Pro Tyr Thr Thr Val Leu Arg Leu Phe Leu Leu Pro<br>                    235                            240                          245 | 1012 |
| CAC AAG GAC CAG CGC CAG ATG TTC TTT GTG ATC AGC CTG GAT CCC CCA<br>His Lys Asp Gln Arg Gln Met Phe Phe Val Ile Ser Leu Asp Pro Pro<br>          250                          255                          260 | 1060 |
| ATC AAG CAA GGC CAA ACT CGC TAC CAC TTC CTG ATC CTC CTC TTC TCC<br>Ile Lys Gln Gly Gln Thr Arg Tyr His Phe Leu Ile Leu Leu Phe Ser<br>                265                          270                        275 | 1108 |
| AAG GAC GAG GAC ATT TCG TTG ACT CTG AAC ATG AAC GAG GAA GTG<br>Lys Asp Glu Asp Ile Ser Leu Thr Leu Asn Met Asn Glu Glu Val<br>280                            285                            290 | 1156 |
| GAG AAG CGC TTT GAG GGT CGG CTC ACC AAG AAC ATG TCA GGA TCC CTC | 1204 |

```
                Glu  Lys  Arg  Phe  Glu  Gly  Arg  Leu  Thr  Lys  Asn  Met  Ser  Gly  Ser  Leu
                295            300                      305                      310

TAT  GAG  ATG  GTC  AGC  CGG  GTC  ATG  AAA  GCA  CTG  GTA  AAC  CGC  AAG  ATC                  1252
Tyr  Glu  Met  Val  Ser  Arg  Val  Met  Lys  Ala  Leu  Val  Asn  Arg  Lys  Ile
                    315                      320                      325

ACA  GTG  CCA  GGC  AAC  TTC  CAA  GGG  CAC  TCA  GGG  GCC  CAG  TGC  ATT  ACC                  1300
Thr  Val  Pro  Gly  Asn  Phe  Gln  Gly  His  Ser  Gly  Ala  Gln  Cys  Ile  Thr
               330                      335                      340

TGT  TCC  TAC  AAG  GCA  AGC  TCA  GGA  CTG  CTC  TAC  CCG  CTG  GAG  CGG  GGC                  1348
Cys  Ser  Tyr  Lys  Ala  Ser  Ser  Gly  Leu  Leu  Tyr  Pro  Leu  Glu  Arg  Gly
               345                      350                      355

TTC  ATC  TAC  GTC  CAC  AAG  CCA  CCT  GTG  CAC  ATC  CGC  TTC  GAT  GAG  ATC                  1396
Phe  Ile  Tyr  Val  His  Lys  Pro  Pro  Val  His  Ile  Arg  Phe  Asp  Glu  Ile
               360                      365                      370

TCC  TTT  GTC  AAC  TTT  GCT  CGT  GGT  ACC  ACT  ACT  ACT  CGT  TCC  TTT  GAC                  1444
Ser  Phe  Val  Asn  Phe  Ala  Arg  Gly  Thr  Thr  Thr  Thr  Arg  Ser  Phe  Asp
375            380                      385                      390

TTT  GAA  ATT  GAG  ACC  AAG  CAG  GGC  ACT  CAG  TAT  ACC  TTC  AGC  AGC  ATT                  1492
Phe  Glu  Ile  Glu  Thr  Lys  Gln  Gly  Thr  Gln  Tyr  Thr  Phe  Ser  Ser  Ile
               395                      400                      405

GAG  AGG  GAG  GAG  TAC  GGG  AAA  CTG  TTT  GAT  TTT  GTC  AAC  GCG  AAA  AAG                  1540
Glu  Arg  Glu  Glu  Tyr  Gly  Lys  Leu  Phe  Asp  Phe  Val  Asn  Ala  Lys  Lys
                    410                      415                      420

CTC  AAC  ATC  AAA  AAC  CGA  GGA  TTG  AAA  GAG  GGC  ATG  AAC  CCA  AGC  TAC                  1588
Leu  Asn  Ile  Lys  Asn  Arg  Gly  Leu  Lys  Glu  Gly  Met  Asn  Pro  Ser  Tyr
               425                      430                      435

GAT  GAA  TAT  GCT  GAC  TCT  GAT  GAG  GAC  CAG  CAT  GAT  GCC  TAC  TTG  GAG                  1636
Asp  Glu  Tyr  Ala  Asp  Ser  Asp  Glu  Asp  Gln  His  Asp  Ala  Tyr  Leu  Glu
               440                      445                      450

AGG  ATG  AAG  GAG  GAA  GGC  AAG  ATC  CGG  GAG  GAG  AAT  GCC  AAT  GAC  AGC                  1684
Arg  Met  Lys  Glu  Glu  Gly  Lys  Ile  Arg  Glu  Glu  Asn  Ala  Asn  Asp  Ser
455                 460                      465                      470

AGC  GAT  GAC  TCA  GGA  GAA  GAA  ACC  GAT  GAG  TCA  TTC  AAC  CCA  GGT  GAA                  1732
Ser  Asp  Asp  Ser  Gly  Glu  Glu  Thr  Asp  Glu  Ser  Phe  Asn  Pro  Gly  Glu
                    475                      480                      485

GAG  GAG  GAA  GAT  GTG  GCA  GAG  GAG  TTT  GAC  AGC  AAC  GCC  TCT  GCC  AGC                  1780
Glu  Glu  Glu  Asp  Val  Ala  Glu  Glu  Phe  Asp  Ser  Asn  Ala  Ser  Ala  Ser
               490                      495                      500

TCC  TCC  AGT  AAT  GAG  GGT  GAC  AGT  GAC  CGG  GAT  GAG  AAG  AAG  CGG  AAA                  1828
Ser  Ser  Ser  Asn  Glu  Gly  Asp  Ser  Asp  Arg  Asp  Glu  Lys  Lys  Arg  Lys
          505                      510                      515

CAG  CTC  AAA  AAG  GCC  AAG  ATG  GCC  AAG  GAC  CGC  AAG  AGC  CGC  AAG  AAG                  1876
Gln  Leu  Lys  Lys  Ala  Lys  Met  Ala  Lys  Asp  Arg  Lys  Ser  Arg  Lys  Lys
     520                      525                      530

CCT  GTG  GAG  GTG  AAG  AAG  GGC  AAA  GAC  CCC  AAT  GCC  CCC  AAG  AGG  CCC                  1924
Pro  Val  Glu  Val  Lys  Lys  Gly  Lys  Asp  Pro  Asn  Ala  Pro  Lys  Arg  Pro
535                 540                      545                      550

ATG  TCT  GCA  TAC  ATG  CTG  TGG  CTC  AAT  GCC  AGC  CGA  GAG  AAG  ATC  AAG                  1972
Met  Ser  Ala  Tyr  Met  Leu  Trp  Leu  Asn  Ala  Ser  Arg  Glu  Lys  Ile  Lys
                    555                      560                      565

TCA  GAC  CAT  CCT  GGC  ATC  AGC  ATC  ACG  GAT  CTT  TCC  AAG  AAG  GCA  GGC                  2020
Ser  Asp  His  Pro  Gly  Ile  Ser  Ile  Thr  Asp  Leu  Ser  Lys  Lys  Ala  Gly
               570                      575                      580

GAG  ATC  TGG  AAG  GGA  ATG  TCC  AAA  GAG  AAG  AAA  GAG  GAG  TGG  GAT  CGC                  2068
Glu  Ile  Trp  Lys  Gly  Met  Ser  Lys  Glu  Lys  Lys  Glu  Glu  Trp  Asp  Arg
               585                      590                      595

AAG  GCT  GAG  GAT  GCC  AGG  AGG  GAC  TAT  GAA  AAA  GCC  ATG  AAA  GAA  TAT                  2116
Lys  Ala  Glu  Asp  Ala  Arg  Arg  Asp  Tyr  Glu  Lys  Ala  Met  Lys  Glu  Tyr
     600                      605                      610

GAA  GGG  GGC  CGA  GGC  GAG  TCT  TCT  AAG  AGG  GAC  AAG  TCA  AAG  AAG  AAG                  2164
```

-continued

| Glu 615 | Gly | Gly | Arg | Gly | Glu 620 | Ser | Ser | Lys | Arg | Asp 625 | Lys | Ser | Lys | Lys | Lys 630 | |
|---|---|---|---|---|---|---|---|---|---|---|---|---|---|---|---|---|
| AAG Lys | AAA Lys | GTA Val | AAG Lys | GTA Val 635 | AAG Lys | ATG Met | GAA Glu | AAG Lys | AAA Lys 640 | TCC Ser | ACG Thr | CCC Pro | TCT Ser | AGG Arg | GGC Gly 645 | 2212 |
| TCA Ser | TCA Ser | TCC Ser | AAG Lys 650 | TCG Ser | TCC Ser | TCA Ser | AGG Arg | CAG Gln 655 | CTA Leu | AGC Ser | GAG Glu | AGC Ser | TTC Phe 660 | AAG Lys | AGC Ser | 2260 |
| AAA Lys | GAG Glu | TTT Phe 665 | GTG Val | TCT Ser | AGT Ser | GAT Asp | GAG Glu 670 | AGC Ser | TCT Ser | TCG Ser | GGA Gly | GAG Glu 675 | AAC Asn | AAG Lys | AGC Ser | 2308 |
| AAA Lys | AAG Lys 680 | AAG Lys | AGG Arg | AGG Arg | AGG Arg | AGC Ser 685 | GAG Glu | GAC Asp | TCT Ser | GAA Glu | GAA Glu 690 | GAA Glu | GAA Glu | CTA Leu | GCC Ala | 2356 |
| AGT Ser 695 | ACT Thr | CCC Pro | CCC Pro | AGC Ser | TCA Ser 700 | GAG Glu | GAC Asp | TCA Ser | GCG Ala | TCA Ser 705 | GGA Gly | TCC Ser | GAT Asp | GAG Glu 710 | TAGAAACG | 2411 |

| | |
|---|---|
| GGAAGGTTCT CTTTGCGCTT GCCTTCTCAC ACCCCCCGAC TCCCCACCCA TATTTTGGTA | 2471 |
| CCAGTTTCTC CTCATGAAAT GCAGTCCCTG GATTCTGTGC CATCTGAACA TGCTCTCCTG | 2531 |
| TTGGTGTGTA TGTCACTAGG GCAGTGGGGA GACGTCTTAA CTCTGCTGCT TCCCAAGGAT | 2591 |
| GGCTGTTTAT AATTTGGGGA GAGATAGGGT GGGAGGCAGG GCAATGCAGG ATCCAAATCC | 2651 |
| TCATCTTACT TTCCCGACCT TAAGGATGTA GCTGCTGCTT GTCCTGTTCA AGTTGCTGGA | 2711 |
| GCAGGGGTCA TGTGAGGCCA GGCCTGTAGC TCCTACCTGG GCCTATTTC TACTTTCATT | 2771 |
| TTGTATTTCT GGTCTGTGAA AATGATTTAA TAAAGGGAAC TGACTTTGGA AACCAAAAAA | 2831 |
| AGGAATTC | 2839 |

( 2 ) INFORMATION FOR SEQ ID NO:2:

( i ) SEQUENCE CHARACTERISTICS:
        ( A ) LENGTH: 709 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: Homo sapiens ( v i i ) IMMEDIATE SOURCE:
        ( B ) CLONE: human SSRP (predicted)

( i x ) FEATURE:
        ( A ) NAME/KEY: Domain
        ( B ) LOCATION: 440..496
        ( D ) OTHER INFORMATION: /label=Acidic ( i x ) FEATURE:
        ( A ) NAME/KEY: Domain
        ( B ) LOCATION: 512..534
        ( D ) OTHER INFORMATION: /label=Basic I ( i x ) FEATURE:
        ( A ) NAME/KEY: Domain
        ( B ) LOCATION: 539..614
        ( D ) OTHER INFORMATION: /label=HMG ( i x ) FEATURE:
        ( A ) NAME/KEY: Domain
        ( B ) LOCATION: 623..640
        ( D ) OTHER INFORMATION: /label=Basic II ( i x ) FEATURE:
        ( A ) NAME/KEY: Domain
        ( B ) LOCATION: 661..709
        ( D ) OTHER INFORMATION: /label=Mixed Charge ( x i ) SEQUENCE DESCRIPTION: SEQ ID NO:2:

```
Met Ala Glu Thr Leu Glu Phe Asn Asp Val Tyr Gln Glu Val Lys Gly
  1               5                  10                  15
Ser Met Asn Asp Gly Arg Leu Arg Leu Ser Arg Gln Gly Ile Ile Phe
                 20                  25                  30
Lys Asn Ser Lys Thr Gly Lys Val Asp Asn Ile Gln Ala Gly Glu Leu
             35                  40                  45
Thr Glu Gly Ile Trp Arg Arg Val Ala Leu Gly His Gly Leu Lys Leu
     50                  55                  60
Leu Thr Lys Asn Gly His Val Tyr Lys Tyr Asp Gly Phe Arg Glu Ser
 65                  70                  75                  80
Glu Phe Glu Lys Leu Ser Asp Phe Phe Lys Thr His Tyr Arg Leu Glu
                 85                  90                  95
Leu Met Glu Lys Asp Leu Cys Val Lys Gly Trp Asn Trp Gly Thr Val
                100                 105                 110
Lys Phe Gly Gly Gln Leu Leu Ser Phe Asp Ile Gly Asp Gln Pro Val
             115                 120                 125
Phe Glu Ile Pro Leu Ser Asn Val Ser Gln Cys Thr Thr Gly Lys Asn
130                 135                 140
Glu Val Thr Leu Glu Phe His Gln Asn Asp Asp Ala Glu Val Ser Leu
145                 150                 155                 160
Met Glu Val Arg Phe Tyr Val Pro Pro Thr Gln Glu Asp Gly Val Asp
                165                 170                 175
Pro Val Glu Ala Phe Ala Gln Asn Val Leu Ser Lys Ala Asp Val Ile
            180                 185                 190
Gln Ala Thr Gly Asp Ala Ile Cys Ile Phe Arg Glu Leu Gln Cys Leu
        195                 200                 205
Thr Pro Arg Gly Arg Tyr Asp Ile Arg Ile Tyr Pro Thr Phe Leu His
210                 215                 220
Leu His Gly Lys Thr Phe Asp Tyr Lys Ile Pro Tyr Thr Thr Val Leu
225                 230                 235                 240
Arg Leu Phe Leu Leu Pro His Lys Asp Gln Arg Gln Met Phe Phe Val
                245                 250                 255
Ile Ser Leu Asp Pro Pro Ile Lys Gln Gly Gln Thr Arg Tyr His Phe
            260                 265                 270
Leu Ile Leu Leu Phe Ser Lys Asp Glu Asp Ile Ser Leu Thr Leu Asn
        275                 280                 285
Met Asn Glu Glu Glu Val Glu Lys Arg Phe Glu Gly Arg Leu Thr Lys
290                 295                 300
Asn Met Ser Gly Ser Leu Tyr Glu Met Val Ser Arg Val Met Lys Ala
305                 310                 315                 320
Leu Val Asn Arg Lys Ile Thr Val Pro Gly Asn Phe Gln Gly His Ser
                325                 330                 335
Gly Ala Gln Cys Ile Thr Cys Ser Tyr Lys Ala Ser Ser Gly Leu Leu
            340                 345                 350
Tyr Pro Leu Glu Arg Gly Phe Ile Tyr Val His Lys Pro Pro Val His
        355                 360                 365
Ile Arg Phe Asp Glu Ile Ser Phe Val Asn Phe Ala Arg Gly Thr Thr
370                 375                 380
Thr Thr Arg Ser Phe Asp Phe Glu Ile Glu Thr Lys Gln Gly Thr Gln
385                 390                 395                 400
Tyr Thr Phe Ser Ser Ile Glu Arg Glu Glu Tyr Gly Lys Leu Phe Asp
                405                 410                 415
```

|       |     |     |     |     |     |     |     |     |     |     |     |     |     |     |
|-------|-----|-----|-----|-----|-----|-----|-----|-----|-----|-----|-----|-----|-----|-----|
| Phe   | Val | Asn | Ala | Lys | Lys | Leu | Asn | Ile | Lys | Asn | Arg | Gly | Leu | Lys | Glu |
|       |     |     | 420 |     |     |     |     | 425 |     |     |     |     | 430 |     |     |
| Gly   | Met | Asn | Pro | Ser | Tyr | Asp | Glu | Tyr | Ala | Asp | Ser | Asp | Glu | Asp | Gln |
|       |     | 435 |     |     |     |     | 440 |     |     |     |     | 445 |     |     |     |
| His   | Asp | Ala | Tyr | Leu | Glu | Arg | Met | Lys | Glu | Glu | Gly | Lys | Ile | Arg | Glu |
|       | 450 |     |     |     |     | 455 |     |     |     |     | 460 |     |     |     |     |
| Glu   | Asn | Ala | Asn | Asp | Ser | Ser | Asp | Asp | Ser | Gly | Glu | Glu | Thr | Asp | Glu |
| 465   |     |     |     |     | 470 |     |     |     |     | 475 |     |     |     |     | 480 |
| Ser   | Phe | Asn | Pro | Gly | Glu | Glu | Glu | Glu | Asp | Val | Ala | Glu | Glu | Phe | Asp |
|       |     |     |     | 485 |     |     |     |     | 490 |     |     |     |     | 495 |     |
| Ser   | Asn | Ala | Ser | Ala | Ser | Ser | Ser | Ser | Asn | Glu | Gly | Asp | Ser | Asp | Arg |
|       |     |     | 500 |     |     |     |     | 505 |     |     |     |     | 510 |     |     |
| Asp   | Glu | Lys | Lys | Arg | Lys | Gln | Leu | Lys | Lys | Ala | Lys | Met | Ala | Lys | Asp |
|       |     | 515 |     |     |     |     | 520 |     |     |     |     | 525 |     |     |     |
| Arg   | Lys | Ser | Arg | Lys | Lys | Pro | Val | Glu | Val | Lys | Lys | Gly | Lys | Asp | Pro |
|       | 530 |     |     |     |     | 535 |     |     |     |     | 540 |     |     |     |     |
| Asn   | Ala | Pro | Lys | Arg | Pro | Met | Ser | Ala | Tyr | Met | Leu | Trp | Leu | Asn | Ala |
| 545   |     |     |     |     | 550 |     |     |     |     | 555 |     |     |     |     | 560 |
| Ser   | Arg | Glu | Lys | Ile | Lys | Ser | Asp | His | Pro | Gly | Ile | Ser | Ile | Thr | Asp |
|       |     |     |     | 565 |     |     |     |     | 570 |     |     |     |     | 575 |     |
| Leu   | Ser | Lys | Lys | Ala | Gly | Glu | Ile | Trp | Lys | Gly | Met | Ser | Lys | Glu | Lys |
|       |     |     | 580 |     |     |     |     | 585 |     |     |     |     | 590 |     |     |
| Lys   | Glu | Glu | Trp | Asp | Arg | Lys | Ala | Glu | Asp | Ala | Arg | Arg | Asp | Tyr | Glu |
|       |     | 595 |     |     |     |     | 600 |     |     |     |     | 605 |     |     |     |
| Lys   | Ala | Met | Lys | Glu | Tyr | Glu | Gly | Gly | Arg | Gly | Glu | Ser | Ser | Lys | Arg |
|       | 610 |     |     |     |     | 615 |     |     |     |     | 620 |     |     |     |     |
| Asp   | Lys | Ser | Lys | Lys | Lys | Lys | Val | Lys | Val | Lys | Met | Glu | Lys | Lys |     |
| 625   |     |     |     |     | 630 |     |     |     |     | 635 |     |     |     | 640 |     |
| Ser   | Thr | Pro | Ser | Arg | Gly | Ser | Ser | Lys | Ser | Ser | Ser | Arg | Gln | Leu |     |
|       |     |     |     | 645 |     |     |     |     | 650 |     |     |     |     | 655 |     |
| Ser   | Glu | Ser | Phe | Lys | Ser | Lys | Glu | Phe | Val | Ser | Ser | Asp | Glu | Ser | Ser |
|       |     |     | 660 |     |     |     |     | 665 |     |     |     |     | 670 |     |     |
| Ser   | Gly | Glu | Asn | Lys | Ser | Lys | Lys | Lys | Arg | Arg | Arg | Ser | Glu | Asp | Ser |
|       |     |     | 675 |     |     |     |     | 680 |     |     |     |     | 685 |     |     |
| Glu   | Glu | Glu | Glu | Leu | Ala | Ser | Thr | Pro | Pro | Ser | Ser | Glu | Asp | Ser | Ala |
|       |     |     | 690 |     |     |     |     | 695 |     |     |     |     | 700 |     |     |
| Ser   | Gly | Ser | Asp | Glu |     |     |     |     |     |     |     |     |     |     |     |
| 705   |     |     |     |     |     |     |     |     |     |     |     |     |     |     |     |

( 2 ) INFORMATION FOR SEQ ID NO:3:

( i ) SEQUENCE CHARACTERISTICS:
        ( A ) LENGTH: 1898 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( v i i ) IMMEDIATE SOURCE:
        ( A ) LIBRARY: Human B cell
        ( B ) CLONE: lambda-Pt1

( x i ) SEQUENCE DESCRIPTION: SEQ ID NO:3:

```
GAATTCCACC AAAACGATGA CGCAGAGGTG TCTCTCATGG AGGTGCGCTT CTACGTCCCA        60
CCCACCCAGG AGGATGGTGT GGACCCTGTT GAGGCCTTTG CCCAGAATGT GTTGTCAAAG       120
```

| GCGGATGTAA | TCCAGGCCAC | GGGAGATGCC | ATCTGCATCT | TCCGGGAGCT | GCAGTGTCTG | 180 |
| ACTCCTCGTG | GTCGTTATGA | CATTCGGATC | TACCCCACCT | TTCTGCACCT | GCATGGCAAG | 240 |
| ACCTTTGACT | ACAAGATCCC | CTACACCACA | GTACTGCGTC | TGTTTTTGTT | ACCCCACAAG | 300 |
| GACCAGCGCC | AGATGTTCTT | TGTGATCAGC | CTGGATCCCC | CAATCAAGCA | AGGCCAAACT | 360 |
| CGCTACCACT | TCCTGATCCT | CCTCTTCTCC | AAGGACGAGG | ACATTTCGTT | GACTCTGAAC | 420 |
| ATGAACGAGG | AAGAAGTGGA | GAAGCGCTTT | GAGGGTCGGC | TCACCAAGAA | CATGTCAGGA | 480 |
| TCCCTCTATG | AGATGGTCAG | CCGGGTCATG | AAAGCACTGG | TAAACCGCAA | GATCACAGTG | 540 |
| CCAGGCAACT | TCCAAGGGCA | CTCAGGGCC | CAGTGCATTA | CCTGTTCCTA | CAAGGCAAGC | 600 |
| TCAGGACTGC | TCTACCCGCT | GGAGCGGGGC | TTCATCTACG | TCCACAAGCC | ACCTGTGCAC | 660 |
| ATCCGCTTCG | ATGAGATCTC | CTTTGTCAAC | TTTGCTCGTG | GTACCACTAC | TACTCGTTCC | 720 |
| TTTGACTTTG | AAATTGAGAC | CAAGCAGGGC | ACTCAGTATA | CCTTCAGCAG | CATTGAGAGG | 780 |
| GAGGAGTACG | GGAAACTGTT | TGATTTTGTC | AACGCGAAAA | AGCTCAACAT | CAAAAACCGA | 840 |
| GGATTGAAAG | AGGGCATGAA | CCCAAGCTAC | GATGAATATG | CTGACTCTGA | TGAGGACCAG | 900 |
| CATGATGCCT | ACTTGGAGAG | GATGAAGGAG | GAAGGCAAGA | TCCGGAGGA | GAATGCCAAT | 960 |
| GACAGCAGCG | ATGACTCAGG | AGAAGAAACC | GATGAGTCAT | TCAACCCAGG | TGAAGAGGAG | 1020 |
| GAAGATGTGG | CAGAGGAGTT | TGACAGCAAC | GCCTCTGCCA | GCTCCTCCAG | TAATGAGGGT | 1080 |
| GACAGTGACC | GGGATGAGAA | GAAGCGGAAA | CAGCTCAAAA | AGGCCAAGAT | GGCCAAGGAC | 1140 |
| CGCAAGAGCC | GCAAGAAGCC | TGTGGAGGTG | AAGAAGGGCA | AAGACCCCAA | TGCCCCCAAG | 1200 |
| AGGCCCATGT | CTGCATACAT | GCTGTGGCTC | AATGCCAGCC | GAGAGAAGAT | CAAGTCAGAC | 1260 |
| CATCCTGGCA | TCAGCATCAC | GGATCTTTCC | AAGAAGGCAG | GCGAGATCTG | GAAGGGAATG | 1320 |
| TCCAAAGAGA | AGAAAGAGGA | GTGGGATCGC | AAGGCTGAGG | ATGCCAGGAG | GGACTATGAA | 1380 |
| AAAGCCATGA | AAGAATATGA | AGGGGGCCGA | GGCGAGTCTT | CTAAGAGGGA | CAAGTCAAAG | 1440 |
| AAGAAGAAGA | AAGTAAAGGT | AAAGATGGAA | AAGAAATCCA | CGCCCTCTAG | GGGCTCATCA | 1500 |
| TCCAAGTCGT | CCTCAAGGCA | GCTAAGCGAG | AGCTTCAAGA | GCAAAGAGTT | TGTGTCTAGT | 1560 |
| GATGAGAGCT | CTTCGGGAGA | GAACAAGAGC | AAAAAGAAGA | GGAGGAGGAG | CGAGGACTCT | 1620 |
| GAAGAAGAAG | AACTAGCCAG | TACTCCCCCC | AGCTCAGAGG | ACTCAGCGTC | AGGATCGAT | 1680 |
| GAGTAGAAAC | GGAGGAAGGT | TCTCTTTGCG | CTTGCCTTCT | CACACCCCCC | GACTCCCCAC | 1740 |
| CCATATTTTG | GTACCAGTTT | CTCCTCATGA | AATGCAGTCC | CTGGATTCTG | TGCCATCTGA | 1800 |
| ACATGCTCTC | CTGTTGGTGT | GTATGTCACT | AGGGCAGTGG | GGAGACGTCT | TAACTCTGCT | 1860 |
| GCTTCCCAAG | GATGGCTGTT | TATAATTTGG | GGAGAGAT | | | 1898 |

( 2 ) INFORMATION FOR SEQ ID NO:4:

( i ) SEQUENCE CHARACTERISTICS:
        ( A ) LENGTH: 1444 base pairs
        ( B ) TYPE: nucleic acid
        ( C ) STRANDEDNESS: double
        ( D ) TOPOLOGY: linear ( i i ) MOLECULE TYPE: cDNA ( v i ) ORIGINAL SOURCE:
        ( A ) ORGANISM: Homo sapiens ( v i i ) IMMEDIATE SOURCE:
        ( A ) LIBRARY: Human B cell
        ( B ) CLONE: lambda Pt2

( x i ) SEQUENCE DESCRIPTION: SEQ ID NO:4:

```
GAATTCCACC AAAACGATGA CGCAGAGGTG TCTCTCATGG AGGTGCGCTT CTACGTCCCA      60
CCCACCCAGG AGGATGGTGT GGACCCTGTT GAGGCCTTTG CCCAGAATGT GTTGTCAAAG     120
GCGGATGTAA TCCAGGCCAC GGGAGATGCC ATCTGCATCT TCCGGGAGCT GCAGTGTCTG     180
ACTCCTCGTG GTCGTTATGA CATTCGGATC TACCCCACCT TTCTGCACCT GCATGGCAAG     240
ACCTTTGACT ACAAGATCCC CTACACCACA GTACTGCGTC TGTTTTTGTT ACCCCACAAG     300
GACCAGCGCC AGATGTTCTT TGTGATCAGC CTGGATCCCC CAATCAAGCA AGGCCAAACT     360
CGCTACCACT TCCTGATCCT CCTCTTCTCC AAGGACGAGG ACATTTCGTT GACTCTGAAC     420
ATGAACGAGG AAGAAGTGGA GAAGCGCTTT GAGGGTCGGC TCACCAAGAA CATGTCAGGA     480
TCCCTCTATG AGATGGTCAG CCGGGTCATG AAAGCACTGG TAAACCGCAA GATCACAGTG     540
CCAGGCAACT TCCAAGGGCA CTCAGGGGCC CAGTGCATTA CCTGTTCCTA CAAGGCAAGC     600
TCAGGACTGC TCTACCCGCT GGAGCGGGGC TTCATCTACG TCCACAAGCC ACCTGTGCAC     660
ATCCGCTTCG ATGAGATCTC CTTTGTCAAC TTTGCTCGTG GTACCACTAC TACTCGTTCC     720
TTTGACTTTG AAATTGAGAC CAAGCAGGGC ACTCAGTATA CCTTCAGCAG CATTGAGAGG     780
GAGGAGTACG GGAAACTGTT TGATTTTGTC AACGCGAAAA AGCTCAACAT CAAAAACCGA     840
GGATTGAAAG AGGGCATGAA CCCAAGCTAC GATGAATATG CTGACTCTGA TGAGGACCAG     900
CATGATGCCT ACTTGGAGAG GATGAAGGAG GAAGGCAAGA TCCGGGAGGA GAATGCCAAT     960
GACAGCAGCG ATGACTCAGG AGAAGAAACC GATGAGTCAT TCAACCCAGG TGAAGAGGAG    1020
GAAGATGTGG CAGAGGAGTT TGACAGCAAC GCCTCTGCCA GCTCCTCCAG TAATGAGGGT    1080
GACAGTGACC GGGATGAGAA GAAGCGGAAA CAGCTCAAAA AGGCCAAGAT GGCCAAGGAC    1140
CGCAAGAGCC GCAAGAAGCC TGTGGAGGTG AAGAAGGGCA AGACCCCAA TGCCCCCAAG    1200
AGGCCCATGT CTGCATACAT GCTGTGGCTC AATGCCAGCC GAGAGAAGAT CAAGTCAGAC    1260
CATCCTGGCA TCAGCATCAC GGATCTTTCC AAGAAGGCAG GCGAGATCTG GAAGGGAATG    1320
TCCAAAGAGA AGAAAGAGGA GTGGGATCGC AAGGCTGAGG ATGCCAGGAG GGACTATGAA    1380
AAAGCCATGA AGAATATGA AGGGGGCCGA GGCGAGTCTT CTAAGAGGGA CAAGTCAAAG    1440
AAGA                                                                1444
```

( 2 ) INFORMATION FOR SEQ ID NO:5:

( i ) SEQUENCE CHARACTERISTICS:
        ( A ) LENGTH: 2384 base pairs
        ( B ) TYPE: nucleic acid
        ( C ) STRANDEDNESS: double
        ( D ) TOPOLOGY: linear ( i i ) MOLECULE TYPE: cDNA ( v i ) ORIGINAL SOURCE:
        ( A ) ORGANISM: Drosophila melanogaster ( v i i ) IMMEDIATE SOURCE:
        ( B ) CLONE: Drosophila SSRP - composite sequence ( v i i i ) POSITION IN GENOME:
        ( A ) CHROMOSOME/SEGMENT: 2
        ( B ) MAP POSITION: 60A 1-4

( i x ) FEATURE:
        ( A ) NAME/KEY: CDS
        ( B ) LOCATION: 123..2291

( x i ) SEQUENCE DESCRIPTION: SEQ ID NO:5:

```
GAATTCCGCG CGCAGTGTTG TTTTGTGTCT GCCGGAATTA TTGTAAATTG GTGACAATTT      60
```

```
CGCAAGGCGG CGTAATACAT AGTTGATCTA TTATCTTGTT ACTGGAGAGG AAGAAGTGCA              120

GG ATG ACA GAC TCT CTG GAG TAC AAC GAC ATA AAC GCC GAA GTG CGC                167
   Met Thr Asp Ser Leu Glu Tyr Asn Asp Ile Asn Ala Glu Val Arg
   1           5               10              15

GGA GTC TTG TGT TCC GGA CGC CTA AAG ATG ACC GAG CAG AAC ATC ATC                215
Gly Val Leu Cys Ser Gly Arg Leu Lys Met Thr Glu Gln Asn Ile Ile
            20              25              30

TTC AAG AAC ACC AAG ACC GGC AAG GTG GAG CAG ATC TCG GCA GAG GAC                263
Phe Lys Asn Thr Lys Thr Gly Lys Val Glu Gln Ile Ser Ala Glu Asp
            35              40              45

ATA GAC CTG ATC AAT TCG CAG AAG TTC GTG GGC ACC TGG GGA CTG AGG                311
Ile Asp Leu Ile Asn Ser Gln Lys Phe Val Gly Thr Trp Gly Leu Arg
        50              55              60

GTG TTC ACC AAA GGC GGC GTG CTC CAC CGC TTC ACC GGA TTC CGC GAC                359
Val Phe Thr Lys Gly Gly Val Leu His Arg Phe Thr Gly Phe Arg Asp
65              70              75

AGC GAG CAC GAG AAG CTG GGC AAG TTT ATC AAG GCT GCC TAC TCG CAG                407
Ser Glu His Glu Lys Leu Gly Lys Phe Ile Lys Ala Ala Tyr Ser Gln
80              85              90              95

GAG ATG GTC GAG AAG GAG ATG TGC GTC AAG GGC TGG AAC TGG GGC ACC                455
Glu Met Val Glu Lys Glu Met Cys Val Lys Gly Trp Asn Trp Gly Thr
            100             105             110

GCC CGC TTC ATG GGC TCC GTC CTG AGC TTC GAC AAG GAG TCG AAG ACC                503
Ala Arg Phe Met Gly Ser Val Leu Ser Phe Asp Lys Glu Ser Lys Thr
            115             120             125

ATC TTC GAG GTG CCG CTG TCG CAC GTT TCG CAG TGC GTG ACC GGC AAG                551
Ile Phe Glu Val Pro Leu Ser His Val Ser Gln Cys Val Thr Gly Lys
        130             135             140

AAC GAG GTC ACC CTG GAG TTC CAC CAA AAC GAC GAT GCG CCC GTG GGT                599
Asn Glu Val Thr Leu Glu Phe His Gln Asn Asp Asp Ala Pro Val Gly
145             150             155

CTA CTG GAG ATG CGG TTC CAC ATA CCC GCC GTG GAG TCG GCC GAG GAG                647
Leu Leu Glu Met Arg Phe His Ile Pro Ala Val Glu Ser Ala Glu Glu
160             165             170             175

GAT CCG GTA GAC AAG TTC CAC CAG AAC GTA ATG AGC AAG GCC TCG GTC                695
Asp Pro Val Asp Lys Phe His Gln Asn Val Met Ser Lys Ala Ser Val
            180             185             190

ATC TCG GCT TCG GGC GAG TCC ATC GCC ATT TTC AGA GAG ATC CAG ATC                743
Ile Ser Ala Ser Gly Glu Ser Ile Ala Ile Phe Arg Glu Ile Gln Ile
            195             200             205

CTC ACG CCT CGC GGT CGC TAT GAC ATC AAG ATC TTC TCG ACC TTC TTC                791
Leu Thr Pro Arg Gly Arg Tyr Asp Ile Lys Ile Phe Ser Thr Phe Phe
        210             215             220

CAG CTG CAC GGC AAG ACG TTC GAC TAC AAG ATT CCC ATG GAC TCG GTG                839
Gln Leu His Gly Lys Thr Phe Asp Tyr Lys Ile Pro Met Asp Ser Val
            225             230             235

CTG CGG CTC TTC ATG CTG CCC CAC AAA GAC AGT CGA CAG ATG TTC TTT                887
Leu Arg Leu Phe Met Leu Pro His Lys Asp Ser Arg Gln Met Phe Phe
240             245             250             255

GTG CTC TCC TTG GAT CCG CCC ATC AAG CAG GGA CAA ACG CGT TAC CAC                935
Val Leu Ser Leu Asp Pro Pro Ile Lys Gln Gly Gln Thr Arg Tyr His
            260             265             270

TAC CTG GTC CTG CTG TTT GCT CCC GAT GAG GAG ACC ACC ATT GAG CTG                983
Tyr Leu Val Leu Leu Phe Ala Pro Asp Glu Glu Thr Thr Ile Glu Leu
            275             280             285

CCA TTC TCG GAA GCC GAG TTG CGA GAC AAG TAC GAG GGC AAG CTG GAG               1031
Pro Phe Ser Glu Ala Glu Leu Arg Asp Lys Tyr Glu Gly Lys Leu Glu
            290             295             300

AAA GAG ATC TCC GGG CCG GTG TAC GAG GTG ATG GGC AAA GTG ATG AAG               1079
Lys Glu Ile Ser Gly Pro Val Tyr Glu Val Met Gly Lys Val Met Lys
```

```
            305                         310                         315
GTG CTG ATC GGT CGA AAA ATT ACC GGA CCC GGT AAC TTT ATC GGA CAC       1127
Val Leu Ile Gly Arg Lys Ile Thr Gly Pro Gly Asn Phe Ile Gly His
320             325                 330                 335

TCT GGC ACG GCT GCA GTG GGC TGC TCG TTC AAG GCT GCA GCT GGA TAT       1175
Ser Gly Thr Ala Ala Val Gly Cys Ser Phe Lys Ala Ala Ala Gly Tyr
                340                 345                 350

CTG TAT CCC CTG GAG CGA GGA TTC ATC TAT ATC CAC AAG CCA CCG CTG       1223
Leu Tyr Pro Leu Glu Arg Gly Phe Ile Tyr Ile His Lys Pro Pro Leu
            355                 360                 365

CAT ATC CGC TTT GAG GAG ATT AGT TCT GTG AAC TTT GCC CGC AGC GGC       1271
His Ile Arg Phe Glu Glu Ile Ser Ser Val Asn Phe Ala Arg Ser Gly
        370                 375                 380

GGA TCC ACG CGA TCT TTC GAC TTC GAA GTG ACG CTC AAG AAC GGA ACT       1319
Gly Ser Thr Arg Ser Phe Asp Phe Glu Val Thr Leu Lys Asn Gly Thr
    385                 390                 395

GTT CAC ATC TTC TCC TCC ATC GAG AAG GAG GAG TAT GCC AAG CTC TTC       1367
Val His Ile Phe Ser Ser Ile Glu Lys Glu Glu Tyr Ala Lys Leu Phe
400                 405                 410                 415

GAC TAC ATC ACA CAG AAG AAG TTG CAT GTC AGC AAC ATG GGC AAG GAC       1415
Asp Tyr Ile Thr Gln Lys Lys Leu His Val Ser Asn Met Gly Lys Asp
                420                 425                 430

AAG AGC GGC TAC AAG GAC GTG GAC TTT GGT GAT TCG GAC AAC GAG AAC       1463
Lys Ser Gly Tyr Lys Asp Val Asp Phe Gly Asp Ser Asp Asn Glu Asn
            435                 440                 445

GAA CCA GAT GCC TAT CTG GCT CGC CTC AAG GCT GAG GCG AGG GAA AAG       1511
Glu Pro Asp Ala Tyr Leu Ala Arg Leu Lys Ala Glu Ala Arg Glu Lys
        450                 455                 460

GAG GAG GAC GAC GAC GAT GGC GAC TCG GAT GAA GAG TCC ACG GAT GAG       1559
Glu Glu Asp Asp Asp Asp Gly Asp Ser Asp Glu Glu Ser Thr Asp Glu
    465                 470                 475

GAC TTC AAG CCC AAC GAG AAC GAG TCC GAT GTG GCC GAG GAG TAT GAC       1607
Asp Phe Lys Pro Asn Glu Asn Glu Ser Asp Val Ala Glu Glu Tyr Asp
480                 485                 490                 495

AGC AAC GTG GAG AGT GAT TCG GAC GAT GAC AGC GAT GCT AGT GGC GGC       1655
Ser Asn Val Glu Ser Asp Ser Asp Asp Ser Asp Ala Ser Gly Gly
                500                 505                 510

GGA GGC GAC AGC GAC GGC GCC AAG AAA AAG AAG GAG AAG AAG TCC GAG       1703
Gly Gly Asp Ser Asp Gly Ala Lys Lys Lys Lys Glu Lys Lys Ser Glu
            515                 520                 525

AAG AAA GAG AAA AAG GAG AAA AAA CAC AAG GAG AAG GAG AGA ACA AAG       1751
Lys Lys Glu Lys Lys Glu Lys Lys His Lys Glu Lys Glu Arg Thr Lys
        530                 535                 540

AAA CCC TCC AAG AAG AAG AAG GAC TCT GGC AAA CCC AAG CGC GCC ACC       1799
Lys Pro Ser Lys Lys Lys Lys Asp Ser Gly Lys Pro Lys Arg Ala Thr
    545                 550                 555

ACC GCT TTC ATG CTC TGG CTG AAC GAC ACG CGC GAG AGC ATC AAG AGG       1847
Thr Ala Phe Met Leu Trp Leu Asn Asp Thr Arg Glu Ser Ile Lys Arg
560                 565                 570                 575

GAA AAT CCG GGC ATA AAG GTT ACC GAG ATC GCC AAG AAG GGC GGC GAG       1895
Glu Asn Pro Gly Ile Lys Val Thr Glu Ile Ala Lys Lys Gly Gly Glu
                580                 585                 590

ATG TGG AAG GAG CTG AAG GAC AAG TCC AAG TGG GAG GAT GCG GCG GCC       1943
Met Trp Lys Glu Leu Lys Asp Lys Ser Lys Trp Glu Asp Ala Ala Ala
            595                 600                 605

AAG GAC AAG CAG CGC TAC CAC GAC GAG ATG CGC AAC TAC AAG CCT GAA       1991
Lys Asp Lys Gln Arg Tyr His Asp Glu Met Arg Asn Tyr Lys Pro Glu
        610                 615                 620

GCG GGC GGT GAC AGC GAC AAC GAG AAG GGT GGA AAG TCC TCC AAG AAG       2039
Ala Gly Gly Asp Ser Asp Asn Glu Lys Gly Gly Lys Ser Ser Lys Lys
```

|  |  |  |  |  |  |  | 625 |  |  | 630 |  |  |  | 635 |  |  |  |
|---|---|---|---|---|---|---|---|---|---|---|---|---|---|---|---|---|---|
| CGC | AAG | ACG | GAG | CCT | TCT | CCA | TCC | AAG | AAG | GCG | AAT | ACC | TCG | GGC | AGC |  | 2087 |
| Arg | Lys | Thr | Glu | Pro | Ser | Pro | Ser | Lys | Lys | Ala | Asn | Thr | Ser | Gly | Ser |  |  |
| 640 |  |  |  |  | 645 |  |  |  |  | 650 |  |  |  |  | 655 |  |  |
| GGC | TTC | AAG | AGC | AAG | GAG | TAC | ATT | TCG | GAC | GAC | GAC | TCC | ACC | AGC | TCC |  | 2135 |
| Gly | Phe | Lys | Ser | Lys | Glu | Tyr | Ile | Ser | Asp | Asp | Asp | Ser | Thr | Ser | Ser |  |  |
|  |  |  |  | 660 |  |  |  |  | 665 |  |  |  |  | 670 |  |  |  |
| GAC | GAC | GAG | AAG | GAC | AAC | GAG | CCT | GCC | AAG | AAG | AAG | AGC | AAG | CCC | CCA |  | 2183 |
| Asp | Asp | Glu | Lys | Asp | Asn | Glu | Pro | Ala | Lys | Lys | Lys | Ser | Lys | Pro | Pro |  |  |
|  |  |  | 675 |  |  |  |  |  | 680 |  |  |  |  | 685 |  |  |  |
| TCC | GAC | GGC | GAT | GCC | AAG | AAG | AAA | AAG | GCC | AAG | AGC | GAG | AGC | GAA | CCG |  | 2231 |
| Ser | Asp | Gly | Asp | Ala | Lys | Lys | Lys | Lys | Ala | Lys | Ser | Glu | Ser | Glu | Pro |  |  |
|  |  | 690 |  |  |  |  | 695 |  |  |  |  | 700 |  |  |  |  |  |
| GAG | GAG | AGC | GAG | GAG | GAC | AGC | AAT | GCC | AGC | GAT | GAG | GAT | GAG | GAA | GAT |  | 2279 |
| Glu | Glu | Ser | Glu | Glu | Asp | Ser | Asn | Ala | Ser | Asp | Glu | Asp | Glu | Glu | Asp |  |  |
| 705 |  |  |  |  | 710 |  |  |  |  | 715 |  |  |  |  |  |  |  |
| GAG | GCC | AGT | GAT | TAGGGCCATA | AACACAACAA | ATCAATTCCA | TAAACACACA |  |  |  |  |  |  |  |  |  | 2331 |
| Glu | Ala | Ser | Asp |  |  |  |  |  |  |  |  |  |  |  |  |  |  |
| 720 |  |  |  |  |  |  |  |  |  |  |  |  |  |  |  |  |  |
| CCACGCTCCT | CACACACCCA | TGTCCCAAAT | CTAGTTTACA | TTCGCCGGAA | TTC |  |  |  |  |  |  |  |  |  |  |  | 2384 |

( 2 ) INFORMATION FOR SEQ ID NO:6:

( i ) SEQUENCE CHARACTERISTICS:
        ( A ) LENGTH: 723 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: Drosophila melanogaster ( v i i ) IMMEDIATE SOURCE:
        ( B ) CLONE: Drosophila SSRP (predicted)

( i x ) FEATURE:
        ( A ) NAME/KEY: Domain
        ( B ) LOCATION: 458..507
        ( D ) OTHER INFORMATION: /label=Acidic ( i x ) FEATURE:
        ( A ) NAME/KEY: Domain
        ( B ) LOCATION: 518..547
        ( D ) OTHER INFORMATION: /label=Basic I ( i x ) FEATURE:
        ( A ) NAME/KEY: Domain
        ( B ) LOCATION: 547..620
        ( D ) OTHER INFORMATION: /label=HMG ( i x ) FEATURE:
        ( A ) NAME/KEY: Domain
        ( B ) LOCATION: 632..649
        ( D ) OTHER INFORMATION: /label=Basic II ( i x ) FEATURE:
        ( A ) NAME/KEY: Domain
        ( B ) LOCATION: 657..723
        ( D ) OTHER INFORMATION: /label=Mixed Charge ( x i ) SEQUENCE DESCRIPTION: SEQ ID NO:6:

| Met | Thr | Asp | Ser | Leu | Glu | Tyr | Asn | Asp | Ile | Asn | Ala | Glu | Val | Arg | Gly |
|---|---|---|---|---|---|---|---|---|---|---|---|---|---|---|---|
| 1 |  |  |  | 5 |  |  |  |  | 10 |  |  |  |  | 15 |  |
| Val | Leu | Cys | Ser | Gly | Arg | Leu | Lys | Met | Thr | Glu | Gln | Asn | Ile | Ile | Phe |
|  |  |  | 20 |  |  |  |  | 25 |  |  |  |  | 30 |  |  |
| Lys | Asn | Thr | Lys | Thr | Gly | Lys | Val | Glu | Gln | Ile | Ser | Ala | Glu | Asp | Ile |
|  |  | 35 |  |  |  |  | 40 |  |  |  |  | 45 |  |  |  |

-continued

| | | | | | | | | | | | | | |
|---|---|---|---|---|---|---|---|---|---|---|---|---|---|
| Asp | Leu 50 | Ile | Asn | Ser | Gln | Lys 55 | Phe | Val | Gly | Thr | Trp 60 | Gly | Leu | Arg | Val |
| Phe 65 | Thr | Lys | Gly | Gly 70 | Val | Leu | His | Arg | Phe | Thr 75 | Gly | Phe | Arg | Asp | Ser 80 |
| Glu | His | Glu | Lys 85 | Leu | Gly | Lys | Phe | Ile 90 | Lys | Ala | Ala | Tyr | Ser 95 | Gln | Glu |
| Met | Val | Glu 100 | Lys | Glu | Met | Cys | Val 105 | Lys | Gly | Trp | Asn | Trp 110 | Gly | Thr | Ala |
| Arg | Phe 115 | Met | Gly | Ser | Val | Leu 120 | Ser | Phe | Asp | Lys | Glu 125 | Ser | Lys | Thr | Ile |
| Phe | Glu 130 | Val | Pro | Leu | Ser | His 135 | Val | Ser | Gln | Cys | Val 140 | Thr | Gly | Lys | Asn |
| Glu 145 | Val | Thr | Leu | Glu | Phe 150 | His | Gln | Asn | Asp | Ala 155 | Pro | Val | Gly | Leu 160 |
| Leu | Glu | Met | Arg | Phe 165 | His | Ile | Pro | Ala | Val 170 | Glu | Ser | Ala | Glu | Glu 175 | Asp |
| Pro | Val | Asp | Lys 180 | Phe | His | Gln | Asn | Val 185 | Met | Ser | Lys | Ala | Ser 190 | Val | Ile |
| Ser | Ala | Ser 195 | Gly | Glu | Ser | Ile | Ala 200 | Ile | Phe | Arg | Glu | Ile 205 | Gln | Ile | Leu |
| Thr | Pro 210 | Arg | Gly | Arg | Tyr | Asp 215 | Ile | Lys | Ile | Phe | Ser 220 | Thr | Phe | Phe | Gln |
| Leu 225 | His | Gly | Lys | Thr | Phe 230 | Asp | Tyr | Lys | Ile | Pro 235 | Met | Asp | Ser | Val | Leu 240 |
| Arg | Leu | Phe | Met | Leu 245 | Pro | His | Lys | Asp | Ser 250 | Arg | Gln | Met | Phe | Phe 255 | Val |
| Leu | Ser | Leu | Asp 260 | Pro | Pro | Ile | Lys | Gln 265 | Gly | Gln | Thr | Arg | Tyr 270 | His | Tyr |
| Leu | Val | Leu | Leu 275 | Phe | Ala | Pro | Asp | Glu 280 | Glu | Thr | Thr | Ile 285 | Glu | Leu | Pro |
| Phe | Ser 290 | Glu | Ala | Glu | Leu | Arg 295 | Asp | Lys | Tyr | Glu | Gly 300 | Lys | Leu | Glu | Lys |
| Glu 305 | Ile | Ser | Gly | Pro | Val 310 | Tyr | Glu | Val | Met | Gly 315 | Lys | Val | Met | Lys | Val 320 |
| Leu | Ile | Gly | Arg | Lys 325 | Ile | Thr | Gly | Pro | Gly 330 | Asn | Phe | Ile | Gly | His 335 | Ser |
| Gly | Thr | Ala | Ala 340 | Val | Gly | Cys | Ser | Phe 345 | Lys | Ala | Ala | Ala | Gly 350 | Tyr | Leu |
| Tyr | Pro | Leu 355 | Glu | Arg | Gly | Phe | Ile 360 | Tyr | Ile | His | Lys | Pro 365 | Pro | Leu | His |
| Ile | Arg 370 | Phe | Glu | Glu | Ile | Ser 375 | Ser | Val | Asn | Phe | Ala 380 | Arg | Ser | Gly | Gly |
| Ser 385 | Thr | Arg | Ser | Phe | Asp 390 | Phe | Glu | Val | Thr | Leu 395 | Lys | Asn | Gly | Thr | Val 400 |
| His | Ile | Phe | Ser | Ser 405 | Ile | Glu | Lys | Glu | Glu 410 | Tyr | Ala | Lys | Leu | Phe 415 | Asp |
| Tyr | Ile | Thr | Gln 420 | Lys | Lys | Leu | His | Val 425 | Ser | Asn | Met | Gly | Lys 430 | Asp | Lys |
| Ser | Gly | Tyr 435 | Lys | Asp | Val | Asp | Phe 440 | Gly | Asp | Ser | Asp | Asn 445 | Glu | Asn | Glu |
| Pro | Asp 450 | Ala | Tyr | Leu | Ala | Arg 455 | Leu | Lys | Ala | Glu | Ala 460 | Arg | Glu | Lys | Glu |
| Glu 465 | Asp | Asp | Asp | Asp | Gly 470 | Asp | Ser | Asp | Glu | Glu 475 | Ser | Thr | Asp | Glu | Asp 480 |

|     |     |     |     |     |     |     |     |     |     |     |     |     |     |     |     |
|-----|-----|-----|-----|-----|-----|-----|-----|-----|-----|-----|-----|-----|-----|-----|-----|
| Phe | Lys | Pro | Asn | Glu | Asn | Ser | Asp | Val | Ala | Glu | Glu | Tyr | Asp | Ser |     |
|     |     |     |     | 485 |     |     |     | 490 |     |     |     |     | 495 |     |     |
| Asn | Val | Glu | Ser | Asp | Ser | Asp | Asp | Ser | Asp | Ala | Ser | Gly | Gly | Gly |     |
|     |     |     | 500 |     |     |     | 505 |     |     |     |     | 510 |     |     |     |
| Gly | Asp | Ser | Asp | Gly | Ala | Lys | Lys | Lys | Glu | Lys | Lys | Ser | Glu | Lys |     |
|     |     |     | 515 |     |     |     | 520 |     |     |     | 525 |     |     |     |     |
| Lys | Glu | Lys | Lys | Glu | Lys | Lys | His | Lys | Glu | Lys | Glu | Arg | Thr | Lys | Lys |
|     | 530 |     |     |     |     | 535 |     |     |     |     | 540 |     |     |     |     |
| Pro | Ser | Lys | Lys | Lys | Lys | Asp | Ser | Gly | Lys | Pro | Lys | Arg | Ala | Thr | Thr |
| 545 |     |     |     |     | 550 |     |     |     |     | 555 |     |     |     |     | 560 |
| Ala | Phe | Met | Leu | Trp | Leu | Asn | Asp | Thr | Arg | Glu | Ser | Ile | Lys | Arg | Glu |
|     |     |     |     | 565 |     |     |     |     | 570 |     |     |     |     | 575 |     |
| Asn | Pro | Gly | Ile | Lys | Val | Thr | Glu | Ile | Ala | Lys | Lys | Gly | Gly | Glu | Met |
|     |     |     |     | 580 |     |     |     | 585 |     |     |     |     | 590 |     |     |
| Trp | Lys | Glu | Leu | Lys | Asp | Lys | Ser | Lys | Trp | Glu | Asp | Ala | Ala | Ala | Lys |
|     |     | 595 |     |     |     |     | 600 |     |     |     |     | 605 |     |     |     |
| Asp | Lys | Gln | Arg | Tyr | His | Asp | Glu | Met | Arg | Asn | Tyr | Lys | Pro | Glu | Ala |
|     | 610 |     |     |     |     | 615 |     |     |     |     | 620 |     |     |     |     |
| Gly | Gly | Asp | Ser | Asp | Asn | Glu | Lys | Gly | Gly | Lys | Ser | Ser | Lys | Lys | Arg |
| 625 |     |     |     |     | 630 |     |     |     |     | 635 |     |     |     |     | 640 |
| Lys | Thr | Glu | Pro | Ser | Pro | Ser | Lys | Lys | Ala | Asn | Thr | Ser | Gly | Ser | Gly |
|     |     |     |     | 645 |     |     |     |     | 650 |     |     |     |     | 655 |     |
| Phe | Lys | Ser | Lys | Glu | Tyr | Ile | Ser | Asp | Asp | Asp | Ser | Thr | Ser | Ser | Asp |
|     |     |     |     | 660 |     |     |     |     | 665 |     |     |     | 670 |     |     |
| Asp | Glu | Lys | Asp | Asn | Glu | Pro | Ala | Lys | Lys | Lys | Ser | Lys | Pro | Pro | Ser |
|     |     | 675 |     |     |     |     | 680 |     |     |     |     | 685 |     |     |     |
| Asp | Gly | Asp | Ala | Lys | Lys | Lys | Ala | Lys | Ser | Glu | Ser | Glu | Pro | Glu |     |
|     | 690 |     |     |     |     | 695 |     |     |     | 700 |     |     |     |     |     |
| Glu | Ser | Glu | Glu | Asp | Ser | Asn | Ala | Ser | Asp | Glu | Asp | Glu | Glu | Asp | Glu |
| 705 |     |     |     |     | 710 |     |     |     |     | 715 |     |     |     |     | 720 |
| Ala | Ser | Asp |     |     |     |     |     |     |     |     |     |     |     |     |     |

( 2 ) INFORMATION FOR SEQ ID NO:7:

( i ) SEQUENCE CHARACTERISTICS:
        ( A ) LENGTH: 3292 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Saccharomyces cerevisiae ( v i i ) IMMEDIATE SOURCE:
        ( B ) CLONE: lambda yPt ( i x ) FEATURE:
        ( A ) NAME/KEY: CDS
        ( B ) LOCATION: 1..1626

( x i ) SEQUENCE DESCRIPTION: SEQ ID NO:7:

| GAA | TTC | GGG | TTT | CAA | GCC | CAG | CCT | CAA | CAA | CAA | CAA | CAG | CAG | CAG | CAG | 48 |
|-----|-----|-----|-----|-----|-----|-----|-----|-----|-----|-----|-----|-----|-----|-----|-----|----|
| Glu | Phe | Gly | Phe | Gln | Ala | Gln | Pro | Gln | Gln | Gln | Gln | Gln | Gln | Gln | Gln |    |
| 1   |     |     |     | 5   |     |     |     |     | 10  |     |     |     |     | 15  |     |    |

| CAA | CAA | CAG | CAA | CAA | CAA | CAA | GCG | CCT | TAT | CAA | GGT | CAC | TTC | CAG | CAG | 96 |
|-----|-----|-----|-----|-----|-----|-----|-----|-----|-----|-----|-----|-----|-----|-----|-----|----|
| Gln | Gln | Gln | Gln | Gln | Gln | Gln | Ala | Pro | Tyr | Gln | Gly | His | Phe | Gln | Gln |    |
|     |     |     | 20  |     |     |     |     | 25  |     |     |     |     | 30  |     |     |    |

| TCG | CCT | CAA | CAA | CAA | CAG | CAA | AAT | GTT | TAT | TTT | CCA | CTA | CCT | CCA | CAA | 144 |

```
            Ser  Pro  Gln  Gln  Gln  Gln  Gln  Asn  Val  Tyr  Phe  Pro  Leu  Pro  Pro  Gln
                      35                       40                      45

TCT  TTG  ACG  CAA  CCT  ACT  TCG  CAG  TCG  CAA  CAA  CAA  CAA  CAA  CAG  TAT       192
Ser  Leu  Thr  Gln  Pro  Thr  Ser  Gln  Ser  Gln  Gln  Gln  Gln  Gln  Gln  Tyr
     50                       55                      60

GCT  AAT  TCG  AAC  TCA  AAT  TCA  AAC  AAC  AAT  GTT  AAT  GTT  AAC  GCG  CTA       240
Ala  Asn  Ser  Asn  Ser  Asn  Ser  Asn  Asn  Asn  Val  Asn  Val  Asn  Ala  Leu
65                       70                      75                            80

CCT  CAG  GAT  TTC  GGT  TAC  ATG  CAA  CAA  ACC  GGA  TCG  GGC  CAA  AAC  TAT       288
Pro  Gln  Asp  Phe  Gly  Tyr  Met  Gln  Gln  Thr  Gly  Ser  Gly  Gln  Asn  Tyr
                      85                       90                      95

CCG  ACG  ATC  AAT  CAA  CAA  CAA  TTT  TCC  GAG  TTT  TAC  AAC  TCC  TTT  TTA       336
Pro  Thr  Ile  Asn  Gln  Gln  Gln  Phe  Ser  Glu  Phe  Tyr  Asn  Ser  Phe  Leu
               100                      105                     110

AGT  CAT  TTA  ACT  CAA  AAA  CAG  ACA  AAC  CCT  TCT  GTC  ACG  GGT  ACA  GGC       384
Ser  His  Leu  Thr  Gln  Lys  Gln  Thr  Asn  Pro  Ser  Val  Thr  Gly  Thr  Gly
          115                     120                     125

GCG  TCT  AGT  AAC  AAC  AAC  AGT  AAC  AAC  AAC  AAT  GTT  AGT  AGC  GGC  AAT       432
Ala  Ser  Ser  Asn  Asn  Asn  Ser  Asn  Asn  Asn  Asn  Val  Ser  Ser  Gly  Asn
     130                     135                     140

AAC  AGC  ACT  AGC  AGT  AAT  CCT  ACC  CAG  CTG  GCA  GCC  TCC  CAA  TTA  AAC       480
Asn  Ser  Thr  Ser  Ser  Asn  Pro  Thr  Gln  Leu  Ala  Ala  Ser  Gln  Leu  Asn
145                     150                     155                           160

CCT  GCC  ACG  GCT  ACT  ACG  GCC  GCC  GCA  AAC  AAT  GCT  GCT  GGC  CCG  GCT       528
Pro  Ala  Thr  Ala  Thr  Thr  Ala  Ala  Ala  Asn  Asn  Ala  Ala  Gly  Pro  Ala
                    165                     170                     175

TCG  TAC  TTG  TCT  CAG  CTC  CCA  CAG  GTG  CAG  AGA  TAC  TAC  CCG  AAC  AAC       576
Ser  Tyr  Leu  Ser  Gln  Leu  Pro  Gln  Val  Gln  Arg  Tyr  Tyr  Pro  Asn  Asn
               180                     185                     190

ATG  AAC  GCT  CTG  TCT  AGT  CTT  TTG  GAC  CCT  TCC  TCT  GCA  GGA  AAT  GCT       624
Met  Asn  Ala  Leu  Ser  Ser  Leu  Leu  Asp  Pro  Ser  Ser  Ala  Gly  Asn  Ala
          195                     200                     205

GCA  GGA  AAT  GCC  AAC  ACC  GCT  ACT  CAT  CCT  GGT  TTG  TTA  CCA  CCC  AAT       672
Ala  Gly  Asn  Ala  Asn  Thr  Ala  Thr  His  Pro  Gly  Leu  Leu  Pro  Pro  Asn
     210                     215                     220

CTG  CAA  CCT  CAA  TTG  ACT  CAC  CAC  CAG  CAG  CAG  ATG  CAG  CAA  CAG  CTG       720
Leu  Gln  Pro  Gln  Leu  Thr  His  His  Gln  Gln  Gln  Met  Gln  Gln  Gln  Leu
225                     230                     235                           240

CAA  TTA  CAA  CAA  CAA  CAG  CAG  TTG  CAG  CAA  CAG  CAG  CAG  CTA  CAA  CAG       768
Gln  Leu  Gln  Gln  Gln  Gln  Gln  Leu  Gln  Gln  Gln  Gln  Gln  Leu  Gln  Gln
                    245                     250                     255

CAA  CAC  CAG  TTG  CAA  CAA  CAA  CAA  CTT  CAA  CAA  CAA  CAT  CAT  CAT             816
Gln  His  Gln  Leu  Gln  Gln  Gln  Gln  Leu  Gln  Gln  Gln  His  His  His
               260                     265                     270

CTA  CAA  CAG  CAA  CAG  CAG  CAA  CAA  CAG  CAT  CCA  GTG  GTG  AAG  AAA  TTA       864
Leu  Gln  Gln  Gln  Gln  Gln  Gln  Gln  Gln  His  Pro  Val  Val  Lys  Lys  Leu
          275                     280                     285

TCT  TCC  ACT  CAA  AGC  AGA  ATT  GAG  AGA  AGA  AAA  CAA  CTG  AAA  AAG  CAA       912
Ser  Ser  Thr  Gln  Ser  Arg  Ile  Glu  Arg  Arg  Lys  Gln  Leu  Lys  Lys  Gln
     290                     295                     300

GGC  CCA  AAG  AGA  CCT  TCT  TCC  GCT  TAT  TTC  CTG  TTT  TCT  ATG  TCC  ATA       960
Gly  Pro  Lys  Arg  Pro  Ser  Ser  Ala  Tyr  Phe  Leu  Phe  Ser  Met  Ser  Ile
305                     310                     315                           320

AGA  AAT  GAG  TTG  CTT  CAA  CAA  TTC  CCT  GAA  GCA  AAG  GTC  CCC  GAA  TTG      1008
Arg  Asn  Glu  Leu  Leu  Gln  Gln  Phe  Pro  Glu  Ala  Lys  Val  Pro  Glu  Leu
                    325                     330                     335

TCT  AAA  TTG  GCT  TCT  GCA  AGG  TGG  AAA  GAG  TTA  ACG  GAT  GAT  CAA  AAA      1056
Ser  Lys  Leu  Ala  Ser  Ala  Arg  Trp  Lys  Glu  Leu  Thr  Asp  Asp  Gln  Lys
               340                     345                     350

AAA  CCA  TTC  TAC  GAA  GAA  TTC  AGA  ACC  AAC  TGG  GAG  AAG  TAC  AGA  GTT      1104
```

-continued

| | | | | | | | | | | | | |
|---|---|---|---|---|---|---|---|---|---|---|---|---|
|Lys|Pro|Phe|Tyr|Glu|Glu|Phe|Arg|Thr|Asn|Trp|Glu|Lys|Tyr|Arg|Val|
| | |355| | | | |360| | | |365| | | | |

```
GTG AGA GAT GCT TAC GAA AAG ACT TTG CCC CCA AAG AGA CCC TCT GGT     1152
Val Arg Asp Ala Tyr Glu Lys Thr Leu Pro Pro Lys Arg Pro Ser Gly
    370             375             380

CCC TTT ATT CAG TTC ACC CAG GAG ATT AGA CCT ACC GTC GTC AAG GAA     1200
Pro Phe Ile Gln Phe Thr Gln Glu Ile Arg Pro Thr Val Val Lys Glu
385             390             395             400

AAT CCT GAT AAA GGT TTA ATC GAA ATT ACC AAG ATA ATC GGT GAA AGA     1248
Asn Pro Asp Lys Gly Leu Ile Glu Ile Thr Lys Ile Ile Gly Glu Arg
            405             410             415

TGG CGC GAG TTA GAC CCC TGC CAA AAG GCG GAA TAC ACT GAA ACT TAC     1296
Trp Arg Glu Leu Asp Pro Cys Gln Lys Ala Glu Tyr Thr Glu Thr Tyr
        420             425             430

AAG AAA AGA TTA AAG GAA TGG GAA AGT TGT TAT CCC GAC GAA AAT GAT     1344
Lys Lys Arg Leu Lys Glu Trp Glu Ser Cys Tyr Pro Asp Glu Asn Asp
    435             440             445

CCA AAC GGT AAC CCA ACC GGT CAC TCA CAT AAG GCC ATG AAC ATG AAT     1392
Pro Asn Gly Asn Pro Thr Gly His Ser His Lys Ala Met Asn Met Asn
450             455             460

TTG AAT ATG GAC ACT AAA ATC ATG GAG AAC CAA GAC AGT ATC GAG CAC     1440
Leu Asn Met Asp Thr Lys Ile Met Glu Asn Gln Asp Ser Ile Glu His
465             470             475             480

ATA ACC GCA AAT GCC ATC GAC TCA GTT ACC GGA AGC AAC AGT AAC AGT     1488
Ile Thr Ala Asn Ala Ile Asp Ser Val Thr Gly Ser Asn Ser Asn Ser
            485             490             495

ACC ACC CCA AAT ACG CCC GTT TCT CCT CCG ATT TCA TTA CAG CAG CAG     1536
Thr Thr Pro Asn Thr Pro Val Ser Pro Pro Ile Ser Leu Gln Gln Gln
        500             505             510

CCG CTC CAA CAA CAA CAA CAA CAG CAG CAA CAA CAA CAA CAC ATG TTA     1584
Pro Leu Gln Gln Gln Gln Gln Gln Gln Gln Gln Gln Gln His Met Leu
    515             520             525

TTG GCT GAC CCC ACT ACA AAT GGT TCG ATC ATA AAA AAT GAA              1626
Leu Ala Asp Pro Thr Thr Asn Gly Ser Ile Ile Lys Asn Glu
530             535             540
```

```
TAACAAATAA ACAACTTTAG TTTTCCACTG TAACATTATC CGACGCAAAC AACGAGAATA   1686
AGGAATTCGA ATTCCTTTTT CAACATTTGT TTAATATTGT ACTACTCTAT TTCCTATTAC   1746
TACAAATTTT ACTTTATTTA ATAATAATTT TTCTTTCCCT TTTTCTAACT TCAGTCTATA   1806
TGTATTTGCC TGTATACATA TACGCATGTG TGTAGTCTTC CCTCCTTCTT GTTTTTGTAA   1866
TATACTTAAG CCAAATTCAA GTTTGCCTCT GATGCTGTGC GAGCTCAACT GACGAGCGTG   1926
ATGAAGCCAA AAAAATTAAT TGATTTCGCC CAGATCGAAC TGGGGATCTG CTGCGTGTTA   1986
AGCAGATCCA TAGCGACTAG ACCACGAAAC CTATTAATCT GTAAATTGA  TCATTTTAAA   2046
GTGGCATAGT TGTACGATAC ACAAGGGCGA CTTATCAACT TACACATAAA TATGTTTGAA   2106
ACATGTCAGA AACACTCGTT ACAAAGCAGA CAAAATTTAT TACATCAAAC GATACCCTGC   2166
CTAGACAAAC CAGTTAAACG TTGTAAATAC CTGGACAACT AGTTTAGTTC CGAGATTCTG   2226
CGCTTCCATT GAGTCTTATG ACTGTTTCTC AGTTTTCATG TCATCTTTTG ACGCCGCATG   2286
GGATAATGTG TACTAATAAC ATAAATACTA GTCAATAGAT GATATTACGA TTCCATCCAC   2346
AAAGGTGAGG TGCTAGTCAC CACCTAAGGA TATTAGATTG TCAAGATGCC CGCTATTACT   2406
GGAGCCCTTA GTATAACGGA TATTTTCAGG ATAGCAGACT TACTTCTCCA AGTGTAAGGG   2466
AACACCGAAT CTAAAGTAGC TACTGCTCCT CCATTCCGTG TATATAATCT TGCTTTTTTT   2526
TAGGAAAATA CTAATACTCG CATATATTGG TTATTATCAT TACTTGGACA CTGTCTGTTC   2586
TATCGCTTCA TTTGTAAATAT GCGTATTGCC CTTCTTATTA ATTGGCTAAT ATTTCACCTG   2646
```

```
CAACATAGGT  CCCTGTTGAT  TAACGTGTTT  ATCCATTTCA  ATCATGAGAA  ATGTTTCTTC    2706

TGTTTTCCAA  TGCCTGGCCG  AGCTGGTAAT  ATATATATAT  ATATGTACAT  AATACTTTAT    2766

TAGATATATT  GTTGATGATT  AGTAGACAAG  TGGTACTACC  AACCGAGAAT  AAAAGCTGGT    2826

CTTCTTATAT  AATATGAGTA  TGGTATAAAT  AGCAGTCACC  GATATCATTG  GTTACCCAAA    2886

GTGACAATTC  ATGTCTTTCA  TAGATATAAA  TCGTAAGCTA  AAATTGAATT  AAAAGATCTT    2946

TAATTTAGCT  GCCCTGCTAA  TCTGAAGTCA  CATATCATTC  CTCATTCTGG  ATCACTCACA    3006

ACATTTATTG  TCTAATAACT  TATGTAATCA  CTATAGTCAC  TGGTGTGAAC  AATGTGAGCA    3066

ATAATAAACC  ACTGTATTAC  CATATACAAA  TGCATATGTT  TAGCCACATA  AGTTTAATTT    3126

ATATTTCTTA  TTTTCCACAC  GATATCCCCA  CTATCAATGA  CATAGATGAT  ATTTCTCCA     3186

CTGGAACAAC  CTGAATACAA  CAATATATTA  TTTGTTCAAG  TACCGCTTCA  GAAATTAAAT    3246

ACTCTGTAAT  TTTGACCCCT  TCTAGCACCA  TATGTACCCC  GAATTC                   3292
```

(2) INFORMATION FOR SEQ ID NO:8:

(i) SEQUENCE CHARACTERISTICS:
        (A) LENGTH: 542 amino acids
        (B) TYPE: amino acid
        (D) TOPOLOGY: linear (ii) MOLECULE TYPE: peptide (vi) ORIGINAL SOURCE:
        (A) ORGANISM: Saccharomyces cerevisiae (vii) IMMEDIATE SOURCE:
        (B) CLONE: fractional yeast SSRP (fySSRP) (predicted)

(xi) SEQUENCE DESCRIPTION: SEQ ID NO:8:

```
Glu Phe Gly Phe Gln Ala Gln Pro Gln Gln Gln Gln Gln Gln Gln Gln
 1               5                  10                  15
Gln Gln Gln Gln Gln Gln Gln Ala Pro Tyr Gln Gly His Phe Gln Gln
                20                  25                  30
Ser Pro Gln Gln Gln Gln Gln Asn Val Tyr Phe Pro Leu Pro Pro Gln
            35                  40                  45
Ser Leu Thr Gln Pro Thr Ser Gln Ser Gln Gln Gln Gln Gln Gln Tyr
    50                  55                  60
Ala Asn Ser Asn Ser Asn Ser Asn Asn Asn Val Asn Val Asn Ala Leu
65                  70                  75                  80
Pro Gln Asp Phe Gly Tyr Met Gln Gln Thr Gly Ser Gly Gln Asn Tyr
                85                  90                  95
Pro Thr Ile Asn Gln Gln Gln Phe Ser Glu Phe Tyr Asn Ser Phe Leu
            100                 105                 110
Ser His Leu Thr Gln Lys Gln Thr Asn Pro Ser Val Thr Gly Thr Gly
    115                 120                 125
Ala Ser Ser Asn Asn Asn Ser Asn Asn Asn Val Ser Ser Gly Asn
130                 135                 140
Asn Ser Thr Ser Ser Asn Pro Thr Gln Leu Ala Ala Ser Gln Leu Asn
145                 150                 155                 160
Pro Ala Thr Ala Thr Thr Ala Ala Ala Asn Asn Ala Ala Gly Pro Ala
                165                 170                 175
Ser Tyr Leu Ser Gln Leu Pro Gln Val Gln Arg Tyr Tyr Pro Asn Asn
            180                 185                 190
Met Asn Ala Leu Ser Ser Leu Leu Asp Pro Ser Ser Ala Gly Asn Ala
    195                 200                 205
```

-continued

```
Ala  Gly  Asn  Ala  Asn  Thr  Ala  Thr  His  Pro  Gly  Leu  Leu  Pro  Pro  Asn
     210                      215                      220
Leu  Gln  Pro  Gln  Leu  Thr  His  His  Gln  Gln  Gln  Met  Gln  Gln  Gln  Leu
225                      230                      235                      240
Gln  Leu  Gln  Gln  Gln  Gln  Gln  Leu  Gln  Gln  Gln  Gln  Gln  Leu  Gln  Gln
               245                      250                           255
Gln  His  Gln  Leu  Gln  Gln  Gln  Gln  Gln  Leu  Gln  Gln  Gln  His  His  His
          260                      265                           270
Leu  Gln  Gln  Gln  Gln  Gln  Gln  Gln  Gln  His  Pro  Val  Val  Lys  Lys  Leu
          275                 280                      285
Ser  Ser  Thr  Gln  Ser  Arg  Ile  Glu  Arg  Arg  Lys  Gln  Leu  Lys  Lys  Gln
     290                 295                      300
Gly  Pro  Lys  Arg  Pro  Ser  Ser  Ala  Tyr  Phe  Leu  Phe  Ser  Met  Ser  Ile
305                      310                 315                           320
Arg  Asn  Glu  Leu  Leu  Gln  Gln  Phe  Pro  Glu  Ala  Lys  Val  Pro  Glu  Leu
               325                      330                           335
Ser  Lys  Leu  Ala  Ser  Ala  Arg  Trp  Lys  Glu  Leu  Thr  Asp  Asp  Gln  Lys
               340                 345                      350
Lys  Pro  Phe  Tyr  Glu  Glu  Phe  Arg  Thr  Asn  Trp  Glu  Lys  Tyr  Arg  Val
          355                 360                      365
Val  Arg  Asp  Ala  Tyr  Glu  Lys  Thr  Leu  Pro  Pro  Lys  Arg  Pro  Ser  Gly
     370                      375                      380
Pro  Phe  Ile  Gln  Phe  Thr  Gln  Glu  Ile  Arg  Pro  Thr  Val  Val  Lys  Glu
385                      390                      395                      400
Asn  Pro  Asp  Lys  Gly  Leu  Ile  Glu  Ile  Thr  Lys  Ile  Ile  Gly  Glu  Arg
               405                      410                           415
Trp  Arg  Glu  Leu  Asp  Pro  Ala  Lys  Lys  Ala  Glu  Tyr  Thr  Glu  Thr  Tyr
               420                 425                      430
Lys  Lys  Arg  Leu  Lys  Glu  Trp  Glu  Ser  Cys  Tyr  Pro  Asp  Glu  Asn  Asp
          435                 440                      445
Pro  Asn  Gly  Asn  Pro  Thr  Gly  His  Ser  His  Lys  Ala  Met  Asn  Met  Asn
     450                      455                      460
Leu  Asn  Met  Asp  Thr  Lys  Ile  Met  Glu  Asn  Gln  Asp  Ser  Ile  Glu  His
465                      470                      475                      480
Ile  Thr  Ala  Asn  Ala  Ile  Asp  Ser  Val  Thr  Gly  Ser  Asn  Ser  Asn  Ser
               485                      490                           495
Thr  Asn  Pro  Asn  Thr  Pro  Val  Ser  Pro  Pro  Ile  Ser  Leu  Gln  Gln  Gln
               500                      505                           510
Pro  Leu  Gln  Gln  Gln  Gln  Gln  Gln  Gln  Gln  Gln  Gln  His  Met  Leu
               515                 520                      525
Leu  Ala  Asp  Pro  Thr  Thr  Asn  Gly  Ser  Ile  Ile  Lys  Asn  Glu
     530                 535                      540
```

USES FOR DNA STRUCTURE-SPECIFIC RECOGNITION PROTEIN

RELATED APPLICATIONS

The following is a continuation-in-part of U.S. Ser. No. 08/258,442, filed Jun. 9, 1994 as a divisional of U.S. Ser. No. 07/814,964 filed Dec. 26, 1991 and now accorded U.S. Pat. No. 5,359,047 and an issue date of Oct. 25, 1994. U.S. Ser. No. 07/814,964 is a continuation-in-part of U.S. Ser. No. 07/539,906 filed Jun. 18, 1990, now abandoned, which was a continuation-in-part of U.S. Ser. No. 07/410,981 filed Sep. 22, 1989, now abandoned which was a continuation-in-part of U.S. Ser. No. 07/247,774 filed Sep. 22, 1988 now abandoned. The teachings of each of the foregoing documents are incorporated herein by reference.

GOVERNMENT SUPPORT

Work described herein was supported by grants from the National Cancer Institute, the National Science Foundation, the National Institutes of Health, the Human Frontier Science Program Organization and a National Research Service Award. The United States Government has certain rights in the invention.

FIELD OF THE INVENTION

The present invention relates generally to risk-assessment of suspected genotoxins, evaluation of novel chemotherapeutic agents, and novel chemotherapeutic methods for cancer management.

BACKGROUND OF THE INVENTION

Cancer arises when a normal cell undergoes neoplastic transformation and becomes a malignant cell. Transformed (malignant) cells escape normal physiologic controls specifying cell phenotype and restraining cell proliferation. Transformed cells in an individual's body thus proliferate, forming a tumor (also referred to as a neoplasm). When a neoplasm is found, the clinical objective is to destroy malignant cells selectively while mitigating any harm caused to normal cells in the individual undergoing treatment. Currently, three major approaches are followed for the clinical management of cancer in humans and other animals. Surgical resection of solid tumors, malignant nodules and or entire organs may be appropriate for certain types of neoplasia. For other types, e.g., those manifested as soluble (ascites) tumors, hematopoeitic malignancies such as leukemia, or where metastasis of a primary tumor to another site in the body is suspected, radiation or chemotherapy may be appropriate. Either of these techniques also is commonly used as an adjunct to surgery. *Harrison's Principles of Internal Medicine*, Part 11 Hematology and Oncology, Ch. 296, 297 and 300-308 (12th ed. 1991).

Chemotherapy is based on the use of drugs that are selectively toxic (cytotoxic) to cancer cells. Id. at Ch. 301. Several general classes of chemotherapeutic drugs have been developed, including drugs that interfere with nucleic acid synthesis, protein synthesis, and other vital metabolic processes. These generally are referred to as antimetabolite drugs. Other classes of chemotherapeutic drugs inflict damage on cellular DNA. Drugs of these classes generally are referred to as genotoxic. Two widely used genotoxic anticancer drugs that have been shown to damage cellular DNA by producing crosslinks therein are cisplatin [cis-diamminedichloroplatinum(II)] and carboplatin [diammine (1,1-cyclobutanedicarboxylato)platinum(II)]. Bruhn et al. (1990), 38 *Prog. Inorg. Chem.* 477, Burnour et al. (1987), 84 *Proc. Natl. Acad. Sci. USA* 3758, Sorenson and Eastman (1987), 48 *Cancer Res.* 4484 and 6703, Pinto and Lippard (1985), 82 *Proc. Natl. Acad. Sci., USA* 4616, Lim and Martini (1984), 38 *J. Inorg. Nucl. Chem.* 119, Lee and Martin (1976), 17 *Inorg. Chim. Acta* 105, Harder and Rosenberg (1970), 6 *Int. J. Cancer* 207, Howle and Gale (1970), 19 *Biochem. Pharmacol* 2757. Cisplatin and/or carboplatin currently are used in the treatment of selected, diverse neoplasms of epithelial and mesenchymal origin, including carcinomas and sarcomas of the respiratory, gastrointestinal and reproductive tracts, of the central nervous system, and of squamous origin in the head and neck. *Harrison's Principles of Internal Medicine* (12th ed. 1991) at Ch. 301. Cisplatin currently is preferred for the management of testicular carcinoma, and in many instances produces a lasting remission. Loehrer and Einhorn (1984), 100 *Ann. Int. Med.* 704. Susceptibility of an individual neoplasm to a desired chemotherapeutic drug or combination thereof often, however, can be accurately assessed only after a trial period of treatment. The time invested in an unsuccessful trial period poses a significant risk in the clinical management of aggressive malignancies.

The repair of damage to cellular DNA is an important biological process carried out by a cell's enzymatic DNA repair machinery. Unrepaired lesions in a cell's genome can impede DNA replication, impair the replication fidelity of newly synthesized DNA or hinder the expression of genes needed for cell survival. Thus, genotoxic drugs generally are considered more toxic to actively dividing cells that engage in DNA synthesis than to quiescent, nondividing cells. Indeed, cells carrying a genetic defect in one or more elements of the enzymatic DNA repair machinery are extremely sensitive to cisplatin. Fraval et al. (1978), 51 *Mutat. Res.* 121, Beck and Brubaker (1973), 116 *J. Bacteriol* 1247. Normal cells of many body tissues, however, are quiescent and commit infrequently to re-enter the cell cycle and divide. Greater time between rounds of cell division generally is afforded for the repair of DNA damage in normal cells inflected by chemotherapeutic genotoxins. As a result, some selectivity is achieved for the killing of cancer cells. Many treatment regimes reflect attempts to improve selectivity for cancer cells by coadministering chemotherapeutic drugs belonging to two or more of these general classes.

In some tissues, however, normal cells divide continuously. Thus, skin, hair follicles, buccal mucosa and other tissues of the gut lining, sperm and blood-forming tissues of the bone marrow remain vulnerable to the action of genotoxic drugs, including cisplatin. These and other classes of chemotherapeutic drugs can also cause severe adverse side effects in drug-sensitive organs, such as the liver and kidneys. These and other adverse side effects seriously constrain the dosage levels and lengths of treatment regimens that can be prescribed for individuals in need of cancer chemotherapy. *Harrison's Principles of Internal Medicine* (12th ed. 1991) at Ch. 301. See also Jones et al. (1985), 52 *Lab. Invest.* 363-374 and Loehrer and Einhorn (1984), 100 *Ann. Int. Med.* 704-714. Such constraints can prejudice the effectiveness of clinical treatment. For example, the drug or drug combination administered must contact and affect cancer cells at times appropriate to impair cell survival. Genotoxic drugs are most effective for killing cancer cells that are actively dividing when chemotherapeutic treatment is applied. Conversely, such drugs are relatively ineffective for the treatment of slow growing neoplasms. Carcinoma cells of the breast, lung and colorectal tissues, for example, typically double as slowly as once every 100 days. *Harrison's Principles of Internal Medicine* (12th ed. 1991) at Table 301-1. Such slowly growing neoplasms present difficult chemotherapeutic targets.

Moreover, cancer cells can acquire resistance to genotoxic drugs through diminished uptake or other changes in drug metabolism, such as those that occur upon drug-induced gene amplification or expression of a cellular gene for multiple drug resistance (MDR). *Harrison's Principles of Internal Medicine* (12th ed. 1991) at Ch. 301. Resistance to genotoxic drugs also can be acquired by activation or enhanced expression of enzymes in the cancer cell's enzymatic DNA repair machinery. Therapies that employ combinations of drugs, or drugs and radiation, attempt to overcome these limitations. The pharmacokinetic profile of each chemotherapeutic drug in such a combinatorial regime, however, will differ. In particular, permeability of neoplastic tissue for each drug will be different. Thus, it can be difficult to achieve genotoxically effective concentrations of multiple chemotherapeutic drugs in target tissues.

Needs remain for additional chemotherapeutic drugs with improved selectivity for destroying transformed cells in situ, without significantly impairing viability of untransformed cells. Needs remain also for enhancing effectiveness of chemotherapeutic drugs, such that satisfactory cell killing can be achieved with lower doses thereof than are currently needed. Thus, needs remain for improved, more accurate methods of testing whether a given chemotherapeutic drug will be effective for killing a particular colony of transformed cells in situ. Poignant needs remain for chemotherapeutic drugs with improved selectivity for destroying transformed cells. Particularly poignant needs remain for ways to render transformed cells selectively more vulnerable to killing through chemotherapy.

SUMMARY OF THE INVENTION

It is an object of this invention to provide a method for assessing whether a suspected genotoxic agent forms lesions in DNA that are bound (recognized) by a DNA structure specific recognition protein (SSRP). Thus, it is an object of this invention to provide an in vitro assay for predicting whether a suspected genotoxic agent forms persistent genomic lesions in eukaryotic cellular DNA.

Another object of this invention is to provide a method for assessing whether a eukaryotic cell contains a DNA structure specific recognition protein that binds to DNA lesions formed by a genotoxic agent. Thus, it is an object of this invention to provide a method for predicting susceptibility of a eukaryotic cell to killing by a genotoxic agent.

Yet another object of this invention is to provide a method of screening new genotoxic drug candidates for the ability to form DNA lesions that are bound by a DNA structure specific recognition protein. Thus, it is an object of this invention to provide a screening method for the rational design of new genotoxic drugs that form persistent genomic lesions in eukaryotic cells. Accordingly, it is an object of this invention to provide new genotoxic drugs identified from the screening method described herein.

Still another object of this invention is to provide a method of causing a eukaryotic cell to express a DNA structure specific recognition protein encoded by a heterologous nucleic acid. Thus, it is an object of this invention to provide a method for enhancing persistence of DNA lesions in the genome of eukaryotic cells. The objects of this invention accordingly include providing a method for sensitizing eukaryotic cells to killing by a genotoxic agent. A further object of this invention therefore includes providing an improved method for killing eukaryotic cells, based on rendering the cells sensitive to a genotoxic agent by causing said cells to express a DNA structure specific recognition protein, and then exposing the cells to the genotoxic agent.

These and other objects, along with advantages and features of the invention disclosed herein, will be apparent from the description, drawings and claims that follow.

The invention described herein rests on the discovery that eukaryotic cells contain one or more intracellular structure specific recognition proteins (SSRPs) that bind to sequence-independent structural motifs in cellular DNA produced by the binding thereto of genotoxic agents. Genotoxic agents or genotoxins bind to or otherwise physically or chemically interact with cellular DNA, causing injury thereto. A site of injury (a lesion) in cellular DNA is referred to herein as a genomic lesion. DNA lesions can include disruptions of the nucleotide sequence, nucleotide basepairing, or distortions of the structure of the DNA double helix. Structural distortion lesions produce three-dimensional DNA structural motifs (e.g., bends, kinks, unwinding, overwinding, non-B helical forms such as A- or Z-DNA, junctions between different helical forms, stem-loop structures, cruciforms, local melting, crossover junctions and the like). Genomic lesions in cellular DNA that are not repaired before the cell commits itself to the cycle of cell division contribute to cell death. Thus, one determinant of a genotoxic agent's cytotoxicity (propensity for contributing to cell death) is the resistance of genomic lesions formed therefrom to cellular repair. Genotoxic agents that form persistent genomic lesions, e.g., lesions that remain in the genome at least until the cell commits to the cell cycle, generally are more effective cytotoxins than agents that form transient, easily repaired genomic lesions. Hence, genotoxic agents that form persistent genomic lesions are preferred for use as chemotherapeutic agents in the clinical management of cancer.

The invention rests more precisely on the discovery, recounted in U.S. Pat. No. 5,359,047 (incorporated herein by reference), that eukaryotic cells contain one or more SSRPs that bind to 1,2-dinucleotide intrastrand adducts of genotoxic metal coordination compounds currently used as chemotherapeutic agents in the clinical management of cancer. Such genotoxic metal coordination compounds include noble metal compounds, such as platinum(II) and platinum (IV) compounds. Typically, the compounds comprise a platinum atom linked to a pair of cis-configured substitutionally labile moieties and a pair of cis-configured electron donor moieties. Binding of the noble metal coordination compounds to nucleic acids occurs upon substitution of the cis-configured labile moieties with atoms of the nucleotide bases, usually adenosine (A) or guanine (G) residues. This produces a crosslink, bridged by the noble metal atom (e.g., platinum) between two vicinal, adjacent or paired nucleotide bases. Platinum-bridged crosslinks between adjacent adenosine and/or guanine residues within a single nucleotide strand (1,2-intrastrand dinucleotide adducts or lesions) of double stranded DNA are abbreviated herein as 1,2-d(A^G) and 1,2-d(G^G) lesions. The class of genotoxic noble metal coordination compounds that form SSRP-recognized genomic lesions includes cisplatin (cis-diamminedichloroplatinum(II) or cis-DDP), carboplatin (diammine(1,1-cyclobutane-dicarboxylato)platinum(II), cis-diamminetetrachloroplatinum(IV), iproplatin (CHIP), DACCP, malonatoplatin, cis-dichloro(ethylenediamine) platinum(II), cis-dichloro(1,2-diaminocyclohexyl)platinum (II), and the like. For convenience, SSRP recognized 1,2-intrastrand dinucleotide adducts formed by any member of this class are referred to herein as cisplatin-type lesions (or adducts).

SSRPs have been shown to bind to the 1,2-d(A^G) or 1,2-d(G^G) intrastrand DNA adducts of cisplatin irrespective of the 5' or 3' orientation of the lesion site and irrespective of the nucleotide sequence adjacent to or comprising the lesion site. Hence, SSRP binding is understood to be sequence-independent, in contrast to the binding properties of other, known nucleic acid binding proteins. SSRP binding to the 1,2-intrastrand dinucleotide adduct (lesion) of a cisplatin-type genotoxic agent results in the formation of a lesioned DNA/SSRP complex. This complex can be detected visually using techniques described in U.S. Pat. No. 5,359,047, including modified Western (Southwestern) blotting and electrophoretic mobility shift analysis (EMSA, also known as bandshift analysis).

SSRPs thus far reported to bind to 1,2-intrastrand cisplatin-type lesions in DNA comprise at least one structural domain generally referred to as an HMG domain. Exemplary, preferred SSRP HMG domains include the HMG domains of human and Drosophila SSRP1, having the sequences set forth, respectively, in amino acid residues 539–614 of Seq. ID No. 2 and residues 547–620 of Seq. ID No. 6. Other useful SSRP HMG domains are encoded by nucleic acids that hybridize specifically, at least under low stringency hybridization conditions such as described in U.S. Pat. No. 5,359,047, to nucleic acid encoding the HMG domain of human or Drosophila SSRP1. SSRPs comprising such HMG domains and occurring in non-human or non-Drosophila eukaryotes are considered homologs of human or Drosophila SSRP1. SSRP-encoding homologous nucleic acids have been detected in diverse eukaryotes, including arthropods (represented by the fruitfly Drosophila melanogaster) and vertebrates including mammals (e.g., human, chimpanzee, monkey, elephant, pig, dog, rabbit, mouse and opossum), aves (e.g., chicken) and fish. It is deduced that homologs of the human and/or Drosophila SSRP occur in numerous eukaryotes, including at least arthropods and vertebrates. A mouse protein comprising an SSRP HMG domain and considered to be a homolog of human SSRP1 has been referred in the literature as T160. SSRP variants occurring within a given eukaryotic species (e.g., humans) that are encoded by nucleic acids comprising sequences similar but not identical to, e.g., residues 539–614 of Seq ID No. 2 (human SSRP1), are understood to be polymorphic or allelic SSRP1 variants. Homologous and polymorphic SSRP1 variants also are useful in the invention described herein.

Proteins comprising still other useful SSRP HMG domains can be identified empirically, based upon their ability to form detectable cisplatin-lesioned DNA/protein complexes. Such other useful SSRP HMG domains need not be encoded by nucleic acid that hybridizes specifically to nucleic acid encoding the HMG domain of human or Drosophila SSRP1. At least one such empirically identified, useful SSRP is fractional yeast SSRP (fySSRP), Seq. ID No. 8. This SSRP has been referred to in publications as IXR-1 (intrastrand crosslink recognition protein 1). Additional useful SSRP HMG domains occur in such known HMG proteins as HMG-1, HMG-2, UBF, LEF-1, SRY, mtTFA, ABF2 and the like. These and other known HMG domain SSRPs have been isolated, variously, from diverse eukaryotes, including human, rodent, Xenopus, Drosophila and yeast.

The consequence of SSRP binding to a genomic lesion is that the sterically large SSRP (or a fragment thereof comprising an HMG domain) becomes localized in the immediate vicinity of the genomic lesion. The SSRP is large enough to sterically obscure (cover) a region of cellular DNA extending from the lesion site in either the 5' and 3' direction for at least about five base pairs, preferably at least about eight base pairs, more preferably at least about twelve base pairs. As a result, lesion-bound SSRP shields the genomic lesion from repair by the cell's enzymatic DNA repair machinery. SSRP-shielded lesions persist in the genome longer than unshielded lesions. SSRP-shielded lesions accordingly are more effective for prejudicing the fidelity of DNA replication, hindering the expression of genes relevant to cell survival, and otherwise contributing to disarray of the cell's nuclear architecture. One or more of the foregoing can contribute to cell death, e.g., by triggering apoptosis.

Certain HMG domain proteins useful herein as SSRPs have been characterized in the literature as transcription factors that control or modulate the expression of one or more cellular genes, including genes that are relevant to cell metabolism or cell secretory function. One such transcription factor is upstream binding factor (UBF), which controls the expression of ribosomal RNA genes and thus is pivotal to the function of the cell's protein synthesis machinery. It is thought that cisplatin-type lesions to which such transcription factors bind as SSRPs mimic or resemble the factor's natural genomic binding site. Binding of such transcription factors to cisplatin-type genomic lesions in effect sequesters the transcription factors at sites other than the natural genomic binding site. Titration of the transcription factors away from their natural genomic binding sites contributes to dysregulation of the controlled genes and therefore contributes to disarray of cellular processes and functions directed by the products (generally proteins, e.g., enzymes) of the controlled genes. For example, sequestration or "hijacking" of the HMG domain transcription factor UBF by cisplatin-type lesions contributes to disarray of cellular protein synthesis, a process needed for cell survival.

The invention described herein accordingly features, in one aspect, a method for predicting cytotoxicity of an agent that binds to DNA (a genotoxic agent or genotoxin). In this method, a sample of double-stranded DNA bearing a lesion formed by the genotoxic agent is contacted with a DNA structure-specific recognition protein, such that a lesioned DNA/SSRP complex forms. This complex is detected or visualized, and optionally quantitated e.g., relative to a standard genotoxic agent known to form a DNA lesion bound by the SSRP. Capacity of the genotoxic agent to form SSRP-shielded DNA lesions in vitro is considered reasonably predictive of competence of the agent to form persistent genomic lesions in cellular DNA, rather than transient, easily repaired lesions.

In another aspect, the invention features a method for assessing cytotoxicity of an agent that inflicts genomic lesions on cellular DNA. That is, the invention features a method for predicting susceptibility of eukaryotic cells to the cytotoxic effects of a genotoxin. In this method, a sample comprising eukaryotic cells is treated so as to release intracellular proteins. The released intracellular proteins are assessed for the presence of one or more DNA structure-specific recognition proteins that bind to DNA lesioned by the genotoxin. Thus, released intracellular proteins are contacted with probe DNA comprising at least one lesion formed the genotoxin, such that a lesioned probe DNA/ cellular SSRP complex forms. This complex is detected or visualized, and optionally quantitated e.g., relative to a standard SSRP known to bind DNA lesions formed by the genotoxic agent. Presence within the eukaryotic cells of one or more SSRPs that bind to the lesioned probe DNA is considered reasonably predictive of formation of persistent genomic lesions in cellular DNA. Accordingly, the presence and amount of SSRPs within the eukaryotic cells can be used to confirm whether a desired genotoxic agent will be cytotoxic to the cells, as well as to assist in the calculation of the dose of genotoxic agent needed to produce the desired degree or rapidity of cell killing.

In yet another aspect, the invention features a method for identifying novel cytotoxic agents that bind to DNA to form genomic lesions. That is, the invention features a screening method for assessing new, genotoxic drug candidates for the ability to form SSRP-recognizable and thus persistent genomic lesions. This method involves contacting a sample of DNA, optionally comprising a detectable moiety, with one or more candidate cytotoxic agents, then incubating the DNA with the candidate under conditions sufficient for DNA binding of genotoxic agents. The DNA bearing a genomic lesion formed by a candidate genotoxin is separated from the incubation mixture comprising unlesioned DNA and unbound candidate. Successfully lesioned DNA is contacted an SSRP under conditions sufficient for the formation of a lesioned DNA/SSRP complex, which is thereupon detected. Optionally, SSRP can be used as an affinity separation agent to isolate successfully lesioned DNA from the incubation mixture. This rational drug screening method can be automated for high-throughput screening of numerous candidate compounds. It is suitable for screening random libraries of compounds, e.g., libraries produced by random or directed combinatorial synthesis of inorganic, organic or biological compounds. The invention accordingly encompasses new cytotoxic agents identified according to the present screening method.

Suitable methods for detecting lesioned DNA/SSRP complexes formed in the above aspects of the present invention include EMSA and Southwestern blotting, both generally according to U.S. Pat. No. 5,359,047. In these and other methods described herein, detection can optionally be facilitated through the use of lesioned probe DNA. Probe DNA is a fragment (e.g., a restriction fragment) of naturally occurring or recombinant DNA, or is a synthetically constructed DNA, of a size suitable for use in standard analytical procedures. For example, the probe DNA is at least about 60 basepairs (bp), preferably at least about 80 bp, more preferably at least about 100 bp in length. Lesioned probe DNA contains at least one structural motif (lesion) produced by the binding thereto of a genotoxic agent. Optionally, the probe DNA also comprises a detectable moiety, such as a radioisotope, chromophore, fluorophore, hapten or other high affinity ligand (e.g., biotin). Other methods for detecting lesioned DNA/SSRP complexes, optionally involving the use of a suitable probe DNA, include nitrocellulose filter retention assay and excinuclease protection assay, both described herein. The nitrocellulose filter retention assay is based upon the selective retention or filter-binding of proteins such as SSRPs. Lesioned probe DNA binds to the SSRP and thus is retained by the filter, whereas unlesioned probe DNA (or probe DNA bearing an unrecognized lesion) flows through or is not retained by the filter. If desired, the filter can be blocked or treated to reduce nonspecific retention. Nitrocellulose filter retention assays can be carried out, e.g., using a standard dot blotting apparatus. The selective retention principle of the nitrocellulose filter retention assay can be enlarged to other affinity based separation or analytical systems, including affinity chromatography systems and the like, through no more than routine experimentation.

The excinuclease protection assay is based directly on the steric hindrance, by bound SSRP, of DNA lesion repair by a eukaryotic DNA repair enzyme. In this assay, the lesioned DNA/SSRP complex is contacted with excinuclease and incubated therewith under conditions sufficient for the excinuclease-catalyzed removal of lesions from DNA. If a DNA lesion is accessible to the excinuclease, a single-stranded nucleic acid fragment comprising the lesion is removed from the double-stranded DNA. Typically, the fragment is less than 30 bp long. The resulting gap is filled with a patch of newly synthesized DNA complementary to the sequence of the unlesioned strand. Using appropriate nucleic acid labeling techniques, described herein, one or more of the nucleic acid products of successful excinuclease repair can be detected. Failure to excise a lesion from DNA, or the degree (e.g., percent) of inhibition thereof indicates SSRP shielding and thus is reasonably correlated with persistence of lesions in the genome.

To facilitate detection of lesioned DNA/SSRP lesions according to the foregoing methods, the invention also provides kits comprising, as applicable, one or more SSRPs, optionally formulated as a cocktail, probe DNA bearing a defined cisplatin-type lesion or in which such a lesion can be produced, a DNA labeling reagent, and optionally a detection or separation reagent selected from an excinuclease preparation and a nitrocellulose filter. Kit components are conveniently packaged for either manual or automated practice of the foregoing methods.

In still another aspect, the invention features a method of sensitizing eukaryotic cells to a genotoxic agent, including a method of rendering eukaryotic cells naturally resistant to cell killing by the genotoxic agent vulnerable thereto. Thus, this aspect of the invention features a method of enhancing cytotoxic effectiveness of a genotoxic agent that normally inflicts only transient lesions on cellular DNA. In this method, eukaryotic cells are contacted with nucleic acid encoding an SSRP that binds to genomic lesions produced by the genotoxic agent, under conditions sufficient for the nucleic acid to be internalized and expressed within said cells. The SSRP-encoding nucleic acid is a foreign (heterologous) nucleic acid, optionally a plasmid, cosmid, expression vector, or virus, e.g., a retrovirus. Intracellular expression of the encoded SSRP enhances persistence of genomic lesions, as the expressed SSRP shields lesions produced by the genotoxic agent from repair by cellular excinuclease. Nucleic acid encoding the SSRP can be caused to internalize within the cells by electroporation or microinjection. Alternatively, where the nucleic acid is present in an expression vector, it can be caused to internalize by transfection according to standard techniques or routine modifications thereof. Optionally, the internalized nucleic acid becomes integrated into the cellular genome. Preferably, the encoded SSRP is overexpressed within the cell, such that an excess of SSRP accumulates, thermodynamically favoring the formation of lesioned DNA/SSRP complexes at the sites of genomic lesions.

Accordingly, yet a further aspect of the invention features an improved method for killing eukaryotic cells. This improved method involves contacting the cells to be killed with nucleic acid encoding an SSRP that binds to lesions in DNA produced by a selected genotoxic agent, under conditions sufficient for the internalization and expression (preferably, overexpression) of the SSRP-encoding nucleic acid within the cells. The method further involves contacting the cells expressing the encoded SSRP with the selected genotoxic agent, under conditions sufficient for the formation of persistent and therefore cytotoxic lesions in the cell genome. Advantageously, then, the invention may allow the use of low doses of the genotoxic agent, formerly considered poorly effective or ineffective for cell killing. The invention also may enhance the effectiveness of additional genotoxins, including genotoxins formerly considered poorly effective or ineffective as cytotoxins. Further, the invention may reconstitute the cytotoxic susceptibility of cells that are refractory to killing by genotoxins, including cells that express a gene for multiple drug resistance.

Eukaryotic cells with which the foregoing methods can be practiced can be cells of a unicellular or multicellular organism. The cells can be maintained in or adapted to culture ex vivo, or can be cells withdrawn from a multicellular organism (e.g., a body fluid sample or tissue biopsy). Alternatively, the cells can be present in vivo in tissue or organs of a multicellular eukaryotic organism. The term, multicellular eukaryotic organism, embraces at least arthropods and vertebrates, including fish, amphibians, birds and mammals, particularly humans. The eukaryotic cells can exhibit either normal or transformed phenotypes. Thus, the eukaryotic cells can be transformed (neoplastic or malignant) cells, including carcinoma cells and sarcoma cells. Transformed mammalian cells with which the present invention can be practiced include transformed cells arising within any body tissue or body compartment, including transformed cells of central or peripheral nervous, mammary, lymphoid, myeloid, cutaneous, respiratory tract, gastrointestinal tract, and urogenital tract origin. To assess susceptibility of transformed cells to killing by a desired chemotherapeutic genotoxin, a sample comprising the transformed cells can be withdrawn from an individual to be treated with the chemotherapeutic agent by standard biopsy techniques and processed for the release of intracellular proteins comprising endogenous SSRPs as described above. If desired, transformed cells can be sensitized to cell killing in situ by the genotoxic agent by causing them to internalize foreign nucleic acid encoding SSRP. Nucleic acid encoding SSRP can be administered to the individual using standard techniques or modifications thereof, appropriate to deliver the nucleic acid to the body compartment, organ or tissue harboring transformed cells. Preferably, the SSRP encoding nucleic acid is internalized by dividing cells, including transformed cells that have escaped normal physiologic and molecular restraints on cell proliferation and cell differentiation. Subsequent exposure of the SSRP-expressing transformed cells to a genotoxic agent according to accepted chemotherapeutic protocols or routine modifications thereof results in preferential killing in situ of the transformed cells.

BRIEF DESCRIPTION OF THE DRAWINGS

The foregoing and other objects, features and advantages of the present invention, as well as the invention itself, will be more fully understood from the following description of preferred embodiments, when read together with the accompanying drawings, in which.

DETAILED DESCRIPTION OF PREFERRED EMBODIMENTS

Figure 1A:
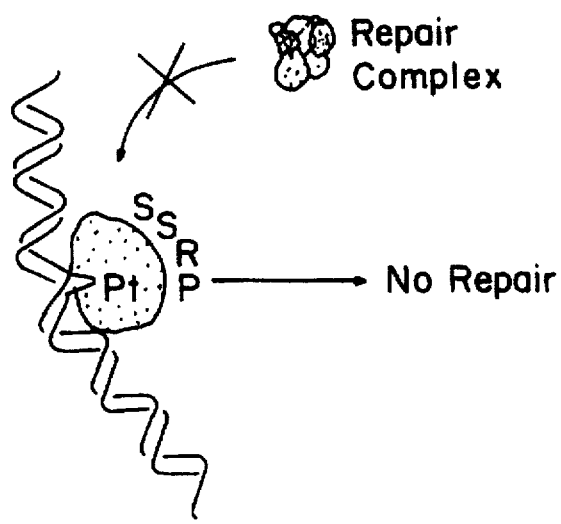
FIG. 1A is a schematic illustration of the steric shielding, by SSRP of a cisplatin-type genomic lesion from repair by the cellular enzymatic DNA repair machinery.

Broadly, the invention capitalizes on the principle that DNA structure specific recognition proteins (SSRPs) contribute to the cytotoxic efficacy of chemotherapeutic genotoxins by binding to toxin-associated genomic lesions and sterically shielding the lesions from repair. That is, lesion-bound SSRP hinders access to the lesion site by elements of the cell's enzymatic DNA repair machinery, including the multisubunit enzyme, excinuclease. This principle is illustrated schematically in FIG. 1A. SSRP-shielded lesions persist in the genome and are more likely than unshielded lesions to contribute to the disarray of cellular metabolism and thus cell death. It is thought that SSRP recognized genomic lesions, although produced by the binding of genotoxic agents to cellular DNA, resemble naturally occurring structural motifs in the genome. Such naturally occurring motifs may be associated with the packaging of cellular DNA in chromatin, or the participation of chromatin in higher ordered aspects of nuclear architecture. Alternatively, such naturally occurring motifs may be associated with DNA replication, gene transcription, transcriptional repression, and like processes involving gene expression.

It has been observed that cisplatin and several of the clinically effective platinum coordination drugs developed subsequent to the discovery of cisplatin comprise a pair of cis-configured, substitutionally labile chloride moieties. Hence, cisplatin-like drugs most likely form DNA adducts that are similar to the well-characterized adducts of cisplatin itself. Lippard et al. (1983), 22 *Biochemistry* 5165. Other platinum coordination compounds, including the trans stereoisomer of cisplatin, lack this pair of cis-configured labile moieties and are largely clinically ineffective. The adduct or lesion formed most frequently by the binding of cisplatin to cellular DNA is the 1,2-intrastrand dinucleotide adduct, in which adjacent nucleotide bases become crosslinked directly through a platinum bridge. 1,2-d(A^G) and 1,2-d (G^G) adducts account together for approximately 90% of the DNA lesions produced in vivo by cisplatin and cisplatin-type drugs. The 1,2-intrastrand cisplatin-type adduct structurally comprises an unwinding element of about 13° at the site of a fairly inflexible bend in the double helix of 32-34° toward the major groove. Bellon and Lippard 1990), 35 *Biophys. Chem.* 179, Rice et al. (1988), 85 *Proc. Natl. Acad. Sci. U.S.A.* 4158. The platinum bridge itself, together with substituents of the platinum atom located trans to the substitutionally labile moieties, projects into the major groove. Efforts have been made to characterize the local unwinding element of cisplatinotype lesions using antinucleoside antibodies. Rice et al. (1988), 85 *Proc. Natl. Acad. Sci. USA* 4158, Sherman and Lippard (1987), 87 *Chem. Rev.* 1153, Sundquist et al. (1986), 25 *Biochemistry* 1520.

Methods described herein arose from the appreciation that eukaryotic proteins comprising one or more HMG domains (Grosschedl et al. (1994), 10 *Trends Genet.* 94, Jantzen et al. (1990), 344 *Nature* 830) bind specifically to 1,2-intrastrand d(G^G) and d(A^G) cisplatin-type DNA adducts, but not to other types of lesions in DNA, even when produced by cisplatin. Bruhn et al. (1992), 89 Proc. Natl. Acad. Sci USA 2307; Pil and Lippard (1992), 256 Science 234. Copending U.S. Ser. No. 08/258,442 and 07/814,964 (now accorded U.S. Pat. No. 5,359,047), the teachings of each of which have been incorporated by reference herein, describe the use of probe DNA bearing cisplatin-type lesions to identify structure specific recognition proteins in eukaryotic cells. A cellular SSRP present in mammalian (human (HeLa) and hamster (V79)) cell extracts bound to double stranded probe DNA bearing lesions produced by cisplatin, cis-dichloro (ethylenediamine)platinum(II) and cis-dichloro(1,2-diaminocyclohexane)platinum(II). The cellular SSRP did not bind unlesioned double stranded or single stranded DNA having the same sequence as the lesioned probe, nor to probe DNA bearing lesions produced by transplatin (the trans isomer of cisplatin) or chloro(diethylenetriamine)platinum (II), neither of which is capable of producing 1,2-intrastrand dinucleotide adducts.

Salient features of the eukaryotic SSRP present in human and hamster cell extracts were characterized by EMSA and Southwestern blotting, both of which allow visualization of lesioned DNA/SSRP complexes in vitro. As described in U.S. Pat. No. 5,359,047, the relative electrophoretic mobility of cellular SSRP, when resolved under standard conditions, was consistent with a molecular mass (Mr) of about 100,000 daltons (d). Further physicochemical characterization confirmed that the cellular SSRP has a sedimentation coefficient, in a standard sucrose gradient, of 5.6S, corresponding to a molecular mass of 91,000 d for an ideal globular protein. Agreement of these two determinations is within acceptable technical limits. The binding constant for formation of the cellular SSRP/lesioned DNA complex was estimated, using competitive EMSA studies, to lie within the range of $(1-20) \times 10^{-10}$ M, indicating a physiologically relevant degree of specificity for cisplatin-type lesions. Thus, functional SSRP occurs and can be detected in cell extracts of eukaryotic cells, including human cells. Standard techniques, or routine modifications thereof, can be applied for releasing intracellular proteins, including functional SSRP, from eukaryotic cells for diagnostic and other purposes within the ambit of this invention.

U.S. Pat. No. 5,359,047 describes the identification, using a Southwestern blot screening technique, of nucleic acid fragments encoding functional regions of the human SSRP. Isolation of two cloned nucleic acid fragments, designated λPt1 and λPt2 (Seq. ID Nos. 3 and 4, respectively), also is reported in Toney et al. (1989), 86 Proc. Natl. Acad. Sci. USA 8328. The fragment encoding an SSRP sequence in λPt1 (Seq. ID No. 3) is 1.88 kilobases (kb) in length; that in λPt2 (Seq. ID No. 4) is 1.44 kb long. E. coli lysogens (Y1089) comprising the longer λPt1 (Seq. ID No. 3) insert were deposited on Sep. 22, 1988 at the American Type Tissue Culture Collection, 12301 Parklawn Drive, Rockville, Md. 20852, USA, under the terms of the Budapest Treaty and assigned accession number 40498. Upon grant of U.S. Pat. No. 5,359,047, all restrictions upon access to this deposit will be removed. Southern blotting and sequencing studies have confirmed that the λPt1 and λPt2 (Seq. ID Nos. 3 and 4, respectively) inserts are aligned at their 5' ends; thus, the entire insert of λPt2 lies within the λPt1 sequence. Either SSRP-encoding nucleic acid fragment can be used as a hybridization probe to detect human or other, homologous SSRPs or variants thereof. The shorter clone λPt2 (Seq. ID Nos. 4), however, is preferred as it more narrowly encompasses the SSRP domain that participates in structure specific recognition of cisplatin-type lesions in DNA. Clone λPt2 (Seq. ID No. 4) was used as a probe in standard Northern blot studies of human and rodent cells to confirm that the eukaryotic cellular SSRP is encoded by homologous 2.8 kb messenger RNAs in at least these representative organisms. From the length of these mRNA transcripts, the intact encoded cellular SSRP should have a molecular mass of 100,000 d. This predicted size correlates well with estimates derived from Southwestern blotting. Northern blotting studies of SSRP expression in various rodent body tissues revealed a pattern consistent with that of a critical gene involved in basic eukaryotic cellular metabolism or survival. SSRP expression did not fluctuate between tissues resistant or susceptible to cisplatin therapy, and did not correlate with the appearance of a cisplatin resistant phenotype in cultured cells.

Figure 2:
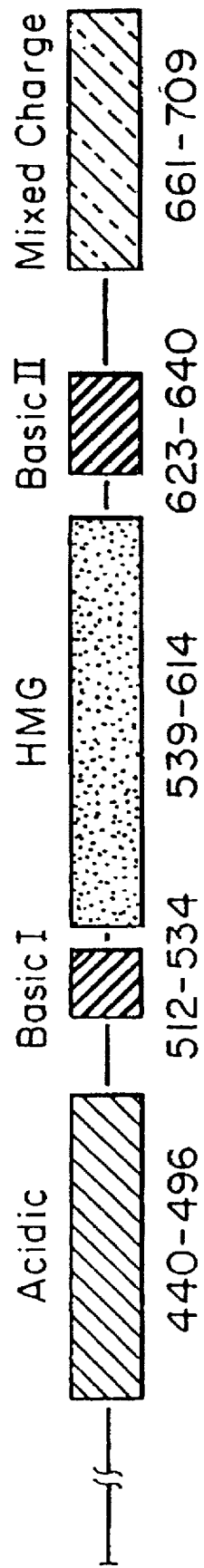
FIG. 2 is a schematic illustration, prepared from the predicted amino acid sequence of the structure specific recognition protein (Seq. ID No. 2) encoded by human SSRP1 gene, showing various domains thereof.

Clone λPt2 (Seq. ID No. 4) also has been used to identify additional SSRP sequences in several human cDNA libraries. As described in U.S. Pat. No. 5,359,047, these overlapping sequences have been aligned as a composite sequence, reconstructing the complete coding sequence for human SSRP1 (Seq. ID No. 1), reported also in Bruhn et al. (1992), 89 Proc. Natl. Acad. Sci. USA 2307, the teachings of which are incorporated by reference herein. The composite nucleic acid sequence, spanning 2839 bp of DNA, comprises a continuous open reading frame of 2310 bp, extending from nucleotide position 275. This open reading frame encodes a protein, human SSRP1, predicted to have the amino acid sequence set forth in Seq. ID No. 2. The λPt1 insert corresponds to nucleotides 725 to 2612 of Seq. ID No. 1, whereas the λPt2 insert corresponds to nucleotides 725 to 2162. The polypeptide expression product of the λPt2 insert corresponds to amino acid residues 149 to 627 of the encoded human SSRP1. The full-length human SSRP1 polypeptide is predicted to be a 710 amino acid protein of molecular weight 81,068 d. Human SSRP1 is predicted to include several highly charged domains, shown schematically in FIG. 2. The acidic domain spanning amino acid residues 440–496, contains 26 negatively charged and 4 positively charged amino acids. This domain has similarity to nucleolin, a factor involved in transcriptional control of rRNA genes. Srivastava et al. (1989), 250 FEBS Lett. 99. Two basic domains (Basic I and Basic II) occupy residues 512–534 and 623–640, respectively. Another highly charged series of amino acid residues lies at the carboxyl terminus, spanning residues 661–709. This domain contains 14 negative and 9 positively charged residues. The hydropathy profile of the encoded protein indicates that the entire region from amino acid residue 400 to the carboxyl terminus is highly hydrophilic.

The predicted sequence of human SSRP1 also comprises a domain spanning amino acid residues 539 to 614, referred to herein as an HMG domain, that has been found to share significant levels of sequence similarity with high mobility group (HMG) 1 and 2 proteins from several eukaryotic species, and with upstream binding factor (UBF), a eukaryotic transcription factor known to comprise an HMG domain and to activate transcription of ribosomal RNA genes. Jantzen et al. (1990), 344 Nature 830, Bustin et al. (1990), 1049 Biochim. Biophys. Acta 231, van Holde (1988) Chromatin (Springer-Verlag, NY), Eink and Bustin (1985), 156 Exp. Cell Res. 295. Optimal alignment between the HMG domain of hSSRP1 and human HMG1, ignoring any sequence discontinuities, revealed a 47% amino acid identity in the regions compared. Comparable levels of sequence similarity also exist between the hSSRP1HMG domain and the corresponding regions of other HMG domain proteins, including sex-determining region Y (SRY), mitochondrial transcription factor II (mtTFII), lymphoid enhancer binding factor I (Lef-1), the T-cell specific transcription factor TCF-1α, the yeast autonomously replicating sequence factor ABF2, and a mouse protein, T160, said to bind to V(D)J recombination signal sequence (RSS) probes. Sinclair et al. (1990), 346 *Nature* 240, Gubbay et al. (1990), 346 *Nature* 245, Parisi and Clayton (1991), 250 *Science* 965, Travis et al. (1991), 5 *Genes & Dev.* 880, Waterman et al. (1991), 5 *Genes & Dev.* 656, Diffley and Stillman (1991), 88 *Proc. Natl. Acad. Sci. USA* 7864, Shirakata et al. (1991), 11 *Mol. Cell. Biol.* 4528. Of these, the T160 protein, which shares 95.5% similarity with hSSRP1, is considered to be the murine homolog of human SSRP1. The expression product of clone λPt2 (Seq. ID No. 4), which binds effectively to cisplatin-type lesions in DNA, includes the acidic domain, Basic I, and the HMG domain of hSSRP1. Of these, the HMG domain is considered to be the functional domain of hSSRP1 that specifically binds to cisplatin-type genomic lesions.

This view is supported by reports that human HMG-1 binds strongly and specifically to cisplatin-modified oligonucleotides. Pil and Lippard (1992), 256 *Science* 234, Hughes et al. (1992), 267 *J. Biol. Chem.* 13520. HMG-1 and -2 are strongly evolutionarily conserved, with homologs identified in diverse eukaryotic genomes, including the human, bovine, porcine, rodent, fish, yeast, maize and protozoan genomes. Wen et al. (1989), 17 *Nucl. Acids Res.* 1197, Pentecost and Dixon (1984), 4 *Biosci. Rep.* 49, Kaplan and Duncan (1988), 16 *Nuc. Acids Res.* 10375, Tsuda et al. (1988), 27 *Biochemistry* 6159, Paonessa et al. (1987), 15 *Nucl. Acids Res.* 9077,; Lee et al. (1987), 15 *Nucl. Acids Res.* 5051, Pentecost et al. (1985), 13 *Nucl. Acids Res.* 4871, Kolodrubetz and Burgum (1990), 265 *J. Biol. Chem.* 3234, Grasser and Feix (1991), 19 *Nucl. Acids Res.* 2573, Roth et al. (1987), 15 *Nucl. Acids Res.* 8112, Hayashi et al. (1989), 105 *J. Biochem.* 577. HMG-1 and -2 have been implicated in DNA processing, particularly in transcriptional regulation, e.g., as reported in Watt and Molloy (1988), 16, *Nucl. Acids Res.* 1471 and Tremethick and Molloy (1986), 261 *J. Bio. Chem.* 6986. Other properties of HMG-1 are consistent with a role in DNA packaging in chromatin. For example, HMG-1 suppresses nucleosome core particle formation, and selectively unwinds negatively supercoiled DNA. Waga et al. (1989), 1007 *Biochim. Biophys. Acta* 209, Sheflin and Spaulding (1989), 28 *Biochemistry* 5658. HMG-1 and -2 also have been shown to bind specifically to structural distortions to DNA such as B-Z junctions and cruciforms. Bianchi et al. (1989), 243 *Science* 1056, Hamada and Bustin (1985), 24 *Biochemistry* 1428. Indeed, HMG-1 has been shown to modify these DNA structural motifs such that transcription in vitro proceeds past these otherwise blocking structures. Waga et al. (1990), 265 *J. Biol. Chem.* 19424, Waga et al. (1988), 153 *Biochem. Biophys. Res. Comm.* 334. Recent studies have established that the HMG-1 protein comprises two domains, each of which is capable independently of binding to four-way junction DNA. Bianchi et al. (1992), 11 *EMBO J.* 1055. This confirms earlier reports that HMG-domain fragments of UBF, Lef-1 and TCF-1α retain the specific DNA binding properties of the corresponding intact transcription factors. Jantzen et al. (1990), 344 *Nature* 830, Giese et al. (1991), 5 *Genes & Devel.* 2567, Waterman et al. 1991), 5 *Genes & Dev.* 656.

Diffley and Stillman (1991), 88 *Proc. Nat. Acad. Sci. USA* 7864, upon considering the known DNA binding properties of HMG-1 and related proteins, suggested that HMG-domain proteins recognize DNA structural motifs rather than sequences. Indeed, HMG-1 and isolated HMG domains thereof now have been shown actively to bend linear duplex DNA, facilitating the in vitro cyclization of substrate DNA by phage T4 DNA ligase. Pil et al. (1993), 90 *Proc. Natl. Acad. Sci. USA* 9465. Similarly, the HMG domain proteins SRY and Lef-1 both have been shown to induce sharp bends, e.g., of approximately 130° , toward the major groove of DNA substrates comprising their respective cognate binding sites. Ferrari et al. (1992), 11 *EMBO J.* 4497, Giese et al. (1992), 69 *Cell* 185. SRY binding to four-way junction DNA is viewed as predominantly structure-specific, rather than sequence dependent. Ferrari et al. (1992), 11 *EMBO J.* 4497. The HMG domains of Lef-1 and SRY contact the DNA double helix predominantly on the minor groove side and actively bend the helix toward the major groove. Giese et al. (1992), 69 *Cell* 185. King and Weiss (1993), 90 *Proc. Natl. Acad. Sci. USA* 11990, have established that the HMG domain of SRY partially intercalates into the widened minor groove at the apex of the recognized or induced bend in substrate duplex DNA. Bending of DNA by the HMG domain spatially approximates linearly distant regions of the double helix. HMG-1, UBF, SRY, Lef-1 and related HMG domain proteins accordingly now are viewed as participating in higher ordered aspects of chromatin structure and nuclear architecture. Wolffe (1994), 264 *Science* 1100, King and Weiss (1993), 90 *Proc. Natl. Acad. Sci. USA* 11990, Ferrari et al. (1992), 11 *EMBO J.* 4497 and Giese et al. 1992), 69 *Cell* 185, the teachings of each of which are incorporated herein by reference. These studies confirm the view consistently expressed in U.S. Ser. Nos. 08/258,442 and 07/814,964 and prior related applications that the 1,2-d(A^G) and 1,2-d(G^G) intrastrand lesions of cisplatin resemble DNA structures that arise naturally within the eukaryotic genome.

Figure 3:
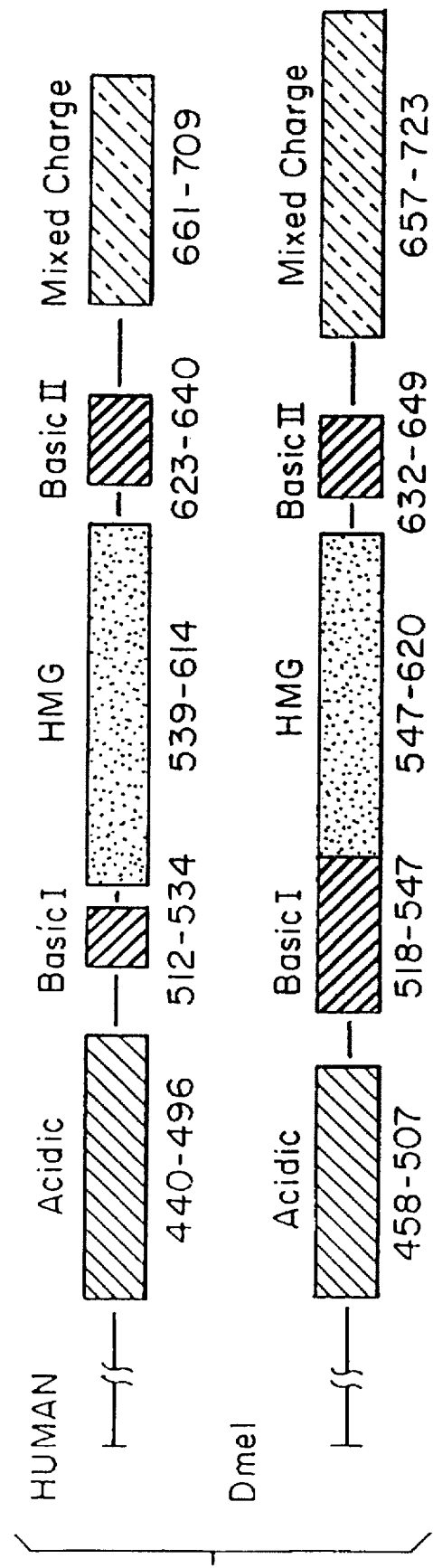
FIG. 3 is a schematic illustration, prepared from the predicted amino acid sequences of the structure specific recognition protein products of the homologous human (Seq. ID No. 2) and D. melanogaster (Dmel, Seq. ID No. 6) SSRP1 genes, showing various domains thereof.

As for HMG-1 and -2, homologs of human SSRP1 occur throughout the eukaryotic phyla. Standard Southern blotting techniques involving detectably labeled λPt2 DNA insert DNA as a probe established that gene sequences encoding homologous SSRPs exist at least in chimpanzee, monkey, elephant, pig, dog, rabbit, mouse, opossum, chicken, fish, and the fruitfly, Drosophila melanogaster. The isolation and cloning of the Drosophila SSRP1 homolog are reported in U.S. Pat. No. 5,359,047 and in Bruhn et al. (1993), 21 *Nucl. Acids Res.* 1643, the teachings of which are incorporated by reference herein. The full length composite nucleic acid sequence encoding Drosophila SSRP1, produced from the alignment of two overlapping cDNA clones, is set forth in Seq. ID No. 5. The Drosophila sequence corresponds to 2384 bp of DNA, and contains large open reading frames in both directions, spanning nucleotides 123–2291 and 2300–600. The larger of the two open reading frames predicts a 723 amino acid protein having a molecular mass of 81,524 d (Seq. ID No. 6). This protein shares extensive sequence similarity with hSSRP1 at both the DNA and protein levels. Sequence similarity also was observed between Drosophila SSRP1 and the above-mentioned members of the eukaryotic HMG domain protein family. Alignment of the human and Drosophila SSRP1 homologs in particular revealed that the presence and order of charged domains therein have been conserved across the 600 million years of evolutionary distance that separate humans from fruitflies. In particular, both phylogenetic counterpart proteins include HMG domains at corresponding locations, shown in FIG. 3. Thus, homologs or phylogenetic counterparts of the human SSRP1 can be isolated as taught in U.S. 5,359,047 and are suitable for use in the present invention.

Homologous SSRPs were not, however, observed upon Southern blot analysis of DNA from the nematode Caenorhabditis elegans, yeast, the parasite Giardia (which retains both prokaryotic and eukaryotic characteristics), or the prokaryotic organisms Pseudomonas and Streptomyces. Bruhn et al. (1993), 21 *Nucl. Acids Res.* 1643. Nonetheless, as taught in U.S. Pat. No. 5,359,047, additional useful structure specific recognition proteins can be isolated empirically, based upon their binding to cisplatin-lesioned probe DNA. The yeast structure specific recognition protein, initially referred to as ySSRP (in U.S. Pat. No. 5,359,047) and later as Ixr-1 (intrastrand crosslink recognition protein 1, Brown et al. (1993), 261 *Science* 603), was isolated in this manner. Seq. ID No. 7 sets forth the nucleic acid sequence of the cloned fragment, λyPt, encoding a functional fragment of the Ixr-1 protein. The encoded amino acid sequence is shown in Seq. ID No. 8. Standard Northern blot analysis of yeast messenger RNAs, using detectably labeled λyPt as a probe, established that Ixr-1 is encoded by a 2.1 kb mRNA, consistent with a translated polypeptide of molecular mass 78,000 d. The central, non-glutamine rich portion of the functional Ixr-1 fragment encoded by λyPt (amino acid residues 282–510) shares sequence similarity with other HMG domain family members, particularly the yeast protein ABF2. ABF2 contains two HMG-boxes and is highly related (37% identical, 65% similar) to ySSRP over 151 of its 183 amino acids. Diffley (1991), 88 *Proc. Nat. Acad. Sci. USA* 7864, has suggested that ABF2 binds to DNA structures, rather than to specific sequences. The isolation of Ixr-1 illustrates that the invention described herein is not limited to the use of hSSRP1 and homologs thereof, but can be practiced with any DNA structure specific recognition protein that specifically binds to cisplatin-type lesions in DNA.

Initially, it was thought that the binding of HMG-domain proteins might aid in damage recognition and thus promote repair of lesions in the genome of eukaryotic cells. Donahue et al. (1990), 29 *Biochemistry* 5872, and subsequent related publications acknowledged that SSRP binding instead might impede the repair of genomic lesions by sterically obscuring the lesion site, hindering access thereto by elements of the cell's enzymatic DNA repair machinery, as depicted in FIG. 1A. From the high estimated binding affinity of eukaryotic cellular SSRP for cisplatin-type lesions, it can be predicted that SSRP-shielded lesions will persist in the genome for longer periods than unshielded genomic lesions. Lesions that are unrepaired for significant periods, e.g., at least until the cell commits to enter or reenter the cell division cycle, contribute to cell death by processes such as apoptosis.

Figure 1B:
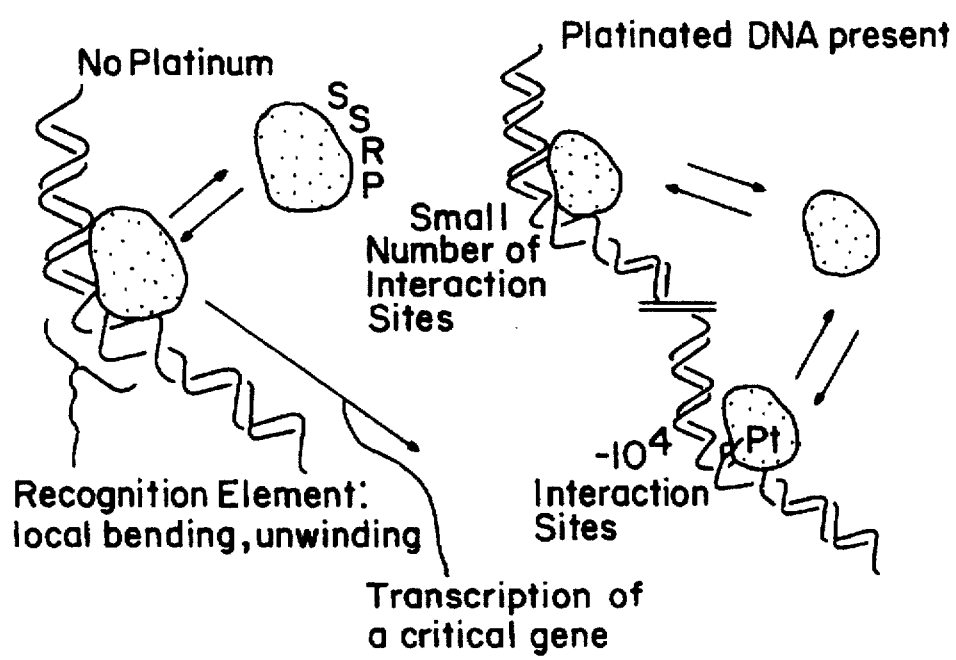
FIG. 1B is a schematic illustration of the titration of SSRP away from its endogenous genomic binding site by cisplatin-type genomic lesion.

A third possible model (shown in FIG. 1B) for the role of SSRPs in cisplatin mediated cell killing, not inconsistent with the repair shielding concept, also was proposed in Donahue et al. (1990), 29 *Biochemistry* 5872. According to this third model, cisplatin-binding SSRPs naturally regulate the function of genes implicated in the emergence of malignancies, or conversely in the maintenance of normal eukaryotic phenotypes. Cisplatin lesions thus provide DNA structural motifs that mimic the natural regulatory sequences of such genes, thereby titrating SSRP away from its natural binding sites in the genome. See also Scovell (1989), A26 *J. Macromol. Sci. Chem.* 455. Effective sequestration of SSRP can be achieved where the protein's binding affinity for cisplatin lesions is within about 1/100 of its binding affinity for the natural genomic binding site. Preferably, the cisplatin lesion affinity is within about 1/10 of that for the natural site; more preferably SSRP binds at least as tightly to cisplatin lesions as to its natural site in the genome. Sequestration by cisplatin lesions therefore "hijacks" SSRP from its natural site in the genome, inducing disarray in cellular processes normally controlled by SSRP. Sequence-independent hijacking of the HMG domain transcription factor hUBF by cisplatin lesions is demonstrated in copending U.S. Ser. No. 08/239,428 (filed 4 May 1994) and reported in Trieber et al. (1994), 91 *Proc. Natl. Acad. Sci. USA* 5672, the teachings of both of which are incorporated herein by reference. The sequence-independent binding affinity of hUBF for cisplatin lesions in DNA was shown to exceed that of HMG-1, and, more pointedly, to far exceed that of the XPAC protein, which recognizes damaged DNA and is essential for human nucleotide excision repair. Jones and Wood (1993), 32 *Biochemistry* 12096. XPAC, therefore, should not displace hUBF from cisplatin lesions. The numbers of intracellular hUBF molecules, and of cisplatin genomic lesions formed per cell during a typical round of chemotherapy, have been calculated. Both are in the range of about $5 \times 10^4$/cell. Bell et al. (1988), 241 *Science* 1192, Reed et al. (1993), 53 *Cancer Res.* 3694. Biologically significant and synergistic assaults on the survival of eukaryotic cells should therefore follow from the cisplatin-hUBF interactions predicted by both the hijacking and shielding models for cisplatin genotoxicity.

The repair recruitment and shielding models originally proposed in Donahue et al. (1990), 29 *Biochemistry* 5872, are based on opposing views of the natural function of SSRP. Gene disruption studies with the yeast SSRP, Ixr-1, provided data consistent with the shielding concept. Thus, Brown et al. (1993), 261 *Science* 603, reported that a mutant strain of yeast carrying homozygous ixr-1 null alleles became two-fold less sensitive to cisplatin killing than the parent (wildtype Ixr-1) strain. Szymkowski et al. (1992), 89 *Proc. Natl. Acad. Sci. USA* 10772, incorporated herein by reference, also supports the view that a cellular SSRP shields 1,2-intrastrand cisplatin-type DNA lesions from repair in eukaryotic cells. HeLa cell extracts, demonstrably competent to repair genomic lesions induced by 2-acetylaminofluorine, were unable to repair a cisplatin 1,2-d(G^G) intrastrand DNA lesion. Prior nicking of substrate DNA comprising the 1,2-d(G^G) lesion, however, rendered this cisplatin lesion susceptible to repair by elements of the HeLa enzymatic DNA repair machinery present in the cell extracts. Id.

Studies disclosed herein, in contrast to earlier circumstantial reports, establish directly that DNA structure specific recognition proteins comprising at least one HMG domain can sterically shield cisplatin-type 1,2-intrastrand DNA adducts from repair by elements of the eukaryotic enzymatic DNA repair machinery. The present studies assess the effects of HMG1 and the human mitochondrial transcription factor h-mtTFA on the excision repair of two defined cisplatin-DNA adducts, the 1,2-intrastrand d(G^G) lesion and the 1,3-intrastrand d(GTG) lesion. Bustin et al. (1990), 1049 *Biochim. Biophys. Acta* 231, Kao et al. (1993), 90 *Proc. Natl. Acad. Sci. USA* 5598, Megraw and Chae (1993), 268 *J. Biol. Chem.* 12758, and Parisi et al. (1993), 13 *Molec. Cell. Biol.* 1951.

Genomic lesions formed by the covalent interaction of DNA with genotoxic drugs, such as cisplatin, are removed from DNA by excinuclease, an ATP-dependent multisubunit enzyme system. Sancar and Tang (1993), 57 *Photochem. Photobiol.* 905, Tanaka and Wood (1994), 19 *Trends Biochem. Sci.* 83. In humans, excinuclease removes covalent lesions in cellular DNA by hydrolyzing the 5th phosphodiester bond 3', and the 22nd–24th phosphodiester bonds 5', to the lesion site, such that 27–29 nucleotide-long oligomers comprising the covalent adduct are excised from the genome. Huang et al. (1992), 89 *Proc. Natl. Acad. Sci. USA* 3664, Svoboda et al. (1993), 268 *J. Biol. Chem.* 1931.

The study described more fully below in EXAMPLE 1 established that, in contrast to the findings of Szymkowski et al. (1992), 89 *Proc. Natl. Acad. Sci. USA* 10772, crude human (HeLa) cell extracts comprising excinuclease can excise cisplatin lesions from DNA. Excision activity was not detected, however, in cell-free extracts from cell lines of two different complementation groups of xeroderma pigmentosum (XP), a human disease characterized by loss of nucleotide exexcision repair capability. Cells from XP patients are sensitive to DNA lesions including thymine dimers and cisplatin adducts. Cleaver and Kraemer (1989), in *Metabolic Basis of Inherited Disease*, 2849 (Scriver et al., Eds.). Mixing of the cell-free extracts from the two different complementation groups restored excision capability (Reardon et al. (1993), 58 *Cold Spring Harbor Symp. Quant. Biol.* 605), a characteristic of the specific action of the multisubunit human excinuclease on damaged DNA. These results indicate that cisplatin lesion repair proceeds by the same enzymatic mechanism as the removal of pyrimidine dimers and psoralen monoadducts from human cellular DNA.

Figure 4:
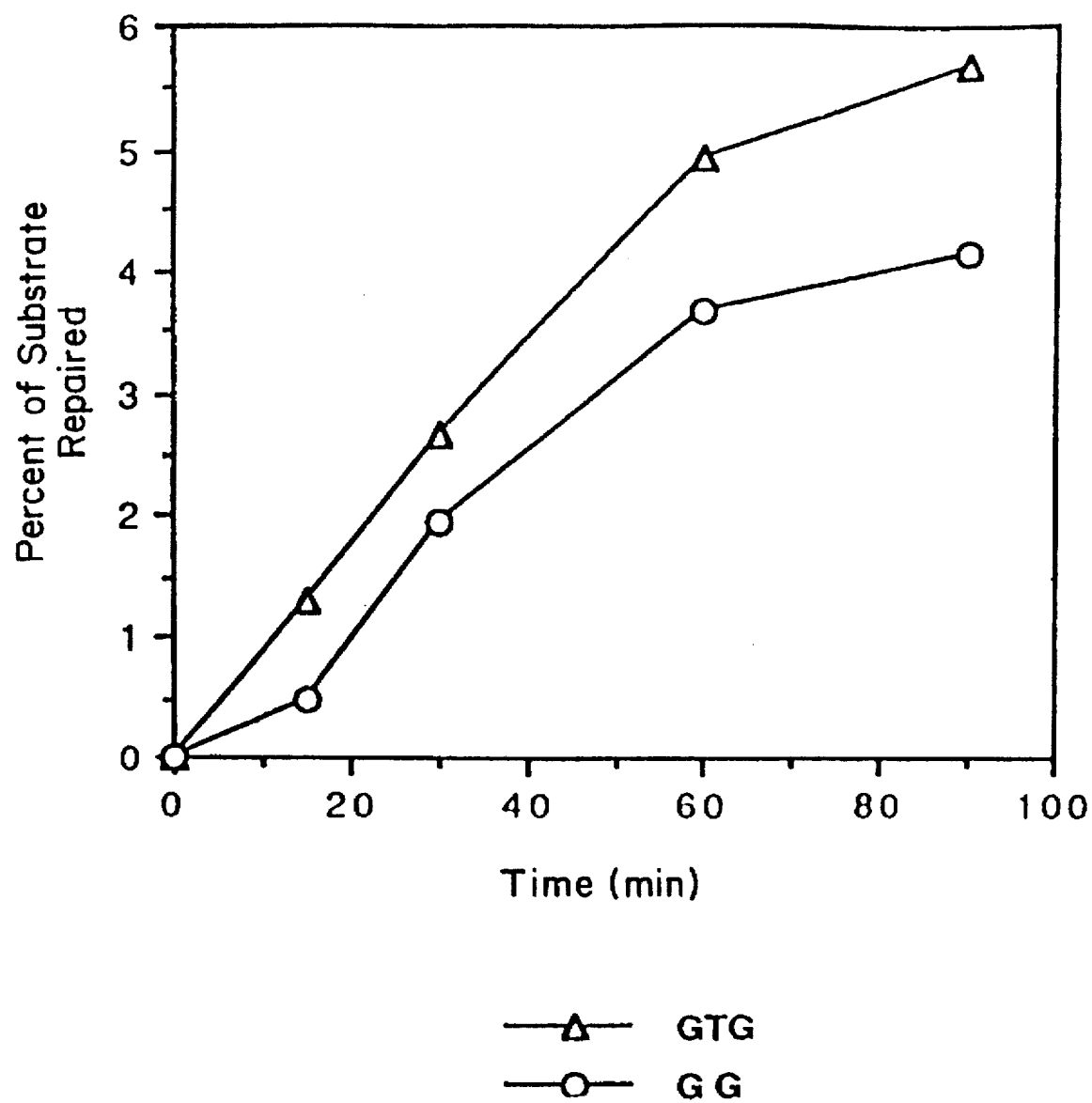
FIG. 4 is a kinetic plot showing the differential rates of excision repair of the 1,3-d(GTG) and 1,2-d(G^G) dinucleotide intrastrand adducts of cisplatin by human cell extracts with excinuclease activity.

Next, timecourse studies were conducted to establish the kinetics of 1,2-d(G^G) and 1,3-d(GTG) cisplatin lesion removal by human exinuclease. EXAMPLE 2, below, discloses that both lesions were repaired, but with different efficiencies. The 1,3-intrastrand crosslink consistently was excised from substrate DNA 30–50% faster than excision of the 1,2-intrastrand crosslink. A kinetic plot of these excision results is shown in FIG. 4. An excinuclease reaction time (30 minutes) within the linear portion of the kinetic plot was selected for further studies of the impact of HMG domain proteins on repair kinetics. It should be noted that the kinetic data shown in FIG. 4 contradict the earlier report of Szymkowski et al. (1992), 89 *Proc. Natl. Acad. Sci. USA* 10772, human (HeLa) cell extracts were unable to repair 1,2-d(G^G) cisplatin lesions in DNA. The excision assay described herein is, however, significantly more sensitive than the repair synthesis assay relied upon in Szymkowski et al. (1992).

Figure 5:
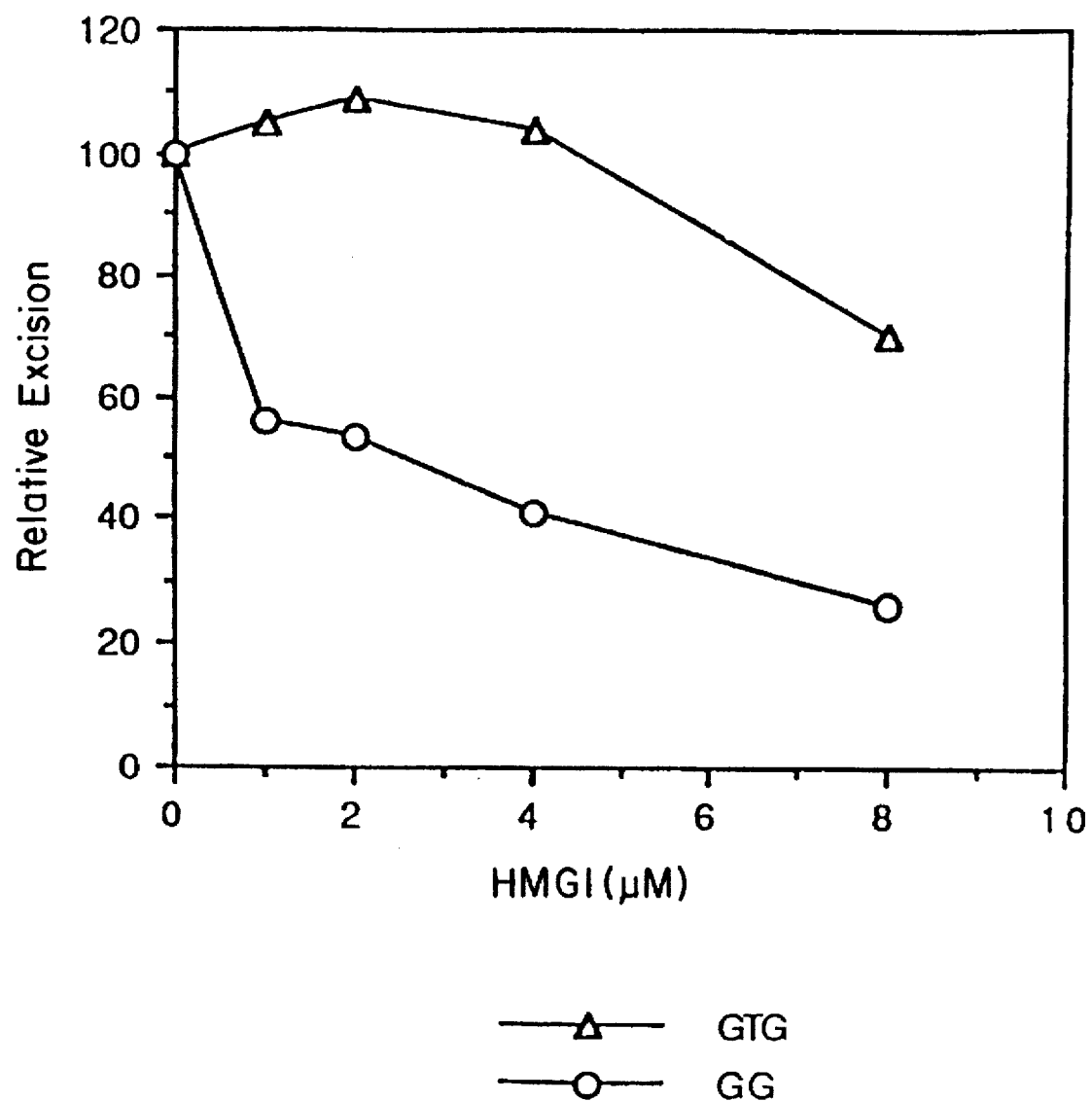
FIG. 5 is a quantitative plot showing that an HMG domain protein (HMG1) differentially shields the cisplatin 1,2-d (G^G) and 1,3-d(GTG) dinucleotide intrastrand adducts from repair by human cell extracts with excinuclease activity.

Pil and Lippard (1992), 256 *Science* 234, reported that HMG1 binds to the 1,2-d(G^G) cisplatin adduct with an affinity significantly in excess of its affinity for the 1,3-d (GTG) cisplatin adduct. Further, the affinity of HMG1 for the latter crosslink was essentially the same as that for unmodified DNA. EXAMPLE 3, below, established that HMG1 not only binds specifically to 1,2-intrastrand adducts: it specifically alters the rate of removal of these DNA lesions by exinuclease. Excision of the cisplatin 1,2-intrastrand crosslink by the exinuclease in HeLa cell-free extract was monotonically inhibited by escalating concentrations of purified HMG1. In contrast, excision of the 1,3-crosslink was modestly stimulated in the presence of HMG1 concentrations up to about 4 µM and then inhibited at higher concentrations. A concentration course plot of these results is shown in FIG. 5. At 4 µM HMG1, both the 1,2- and the 1,3-intrastrand crosslinked substrates were saturated with HMG1, yet only excision of the 1,2-d(G^G) crosslink was inhibited. Therefore, only the specific mode of HMG binding interferes with the excision repair of cisplatin lesions. The stimulatory effect observed for excision of the 1,3-intrastrand crosslink might be attributable to HMG1-mediated bending of the DNA (Bianchi et al. (1989), 243 *Science* 1056) in a manner favorable for the excinuclease. Only at very high concentrations of HMG1 (in excess of 4 µM) did non-specific binding interfere with repair.

Another HMG domain protein, human mitochondrial transcription factor A (h-mtTFA) also has been shown to bind, in a sequence independent manner, to cisplatin-type 1,2-intrastrand dinucleotide lesions in DNA, as assessed by EMSA and Southwestern blotting. This member of the SSRP family also is shown herein to selectively shield the 1,2-d (G^G) intrastrand adduct from repair by human excinuclease. Indeed, h-mtTFA bound to the 1,2-d(G^G) lesion with greater affinity than HMG1. TABLE 1, below, discloses that 0.5 µM concentrations of h-mtTFA inhibited excision of the 1,2-intrastrand cisplatin adduct by 95% while blocking removal of the 1,3-d(GTG) crosslink by only 40%. The same molar concentration of HMG1 achieved only about 20% repair shielding.

EXAMPLES 3 and 4 directly demonstrate that two distinct HMG domain proteins within the SSRP family bind with specificity to the major DNA adduct of cisplatin produced in vivo (the 1,2-intrastrand d(G^G) adduct; see Fichtinger-Schepman et al. (1985), 24 *Biochemistry* 707; Eastman (1987), 34 *Pharmacol. Ther.* 155. Specific binding produces a DNA-protein complex at the lesion site that effectively shields the lesion from excinuclease activity. These results confirm early indications in Brown et al. (1993), 261 *Science* 603 and Trieber et al. (1994), 91 *Proc. Natl. Acad. Sci. USA* 5672, that any eukaryotic protein that comprises at least one HMG domain that binds with high, specific affinity to cisplatin-type 1,2-intrastrand lesions in DNA can shield these genomic lesions from repair, thereby enhancing persistence of cisplatin-type lesions in the genome in vivo. Shielded lesions persist in the genome, disrupting the transcription of cellular genes and impeding DNA synthesis associated with cell replication. Shielding by the full range of HMG domain proteins present intracellularly, rather than by hSSRP1 or a homolog thereof alone, therefore contributes to the sensitivity of tumors to cisplatin chemotherapy. Accordingly, the entire spectrum of intracellular cisplatin lesion binding SSRPs can be assessed to gauge the cytotoxic efficacy of cisplatin and related chemotherapeutic drugs.

Results presented herein further explain the longstanding conundrum presented by observations that hSSRP1 expression patterns do not correlate with the sensitivities of various eukaryotic tissues and cell lines to cisplatin. Bruhn et al. (1992), 89 *Proc. Natl. Acad. Sci USA* 2307. The concentrations of HMG domain SSRPs used in the EXAMPLE 3 and 4 studies were significantly higher than the endogenous cellular concentration of each respective protein. However, there are many known HMG domain SSRPs, and possibly many yet to be discovered. Many of these endogenous HMG domain proteins may act in concert to shield cisplatin lesions from repair in vivo. Thus, measurement of the total concentration of intracellular HMG domain proteins should provide a reasonably accurate predictor of the sensitivity of particular cell and tissue types to cisplatin. Preferably, this value can be weighted for the relative affinities of major endogenous SSRPs for the 1,2-intrastrand crosslink, or for intracellular compartmentalization affects on the accessibility of cisplatin lesions to particular endogenous SSRPs. The total endogenous concentration of HMG domain proteins that bind cisplatin-type genomic lesions may match or even exceed the concentrations of purified individual HMG domain proteins used in EXAMPLES 3 and 4.

Further, the in vitro assay system described in EXAMPLES 3 and 4 can be used as the basis for preliminary testing, in cell free systems, of novel cisplatin analogs or other chemotherapeutic drug candidates. It has been established that cisplatin and related drugs produce lesions in DNA through covalent bonds formed upon hydrolysis of the bonds linking the chlorine and platinum atoms, and subsequent establishment of bonds linking the platinum atom to two purine bases. Following DNA adduct formation, the amine groups bonded to the platinum atom in cisplatin protrude into the major groove. HMG domain SSRPs, however, bind to recognized DNA lesions predominantly on the minor groove side, opposite to the platinum bridge. Neither the platinum atom itself nor electron donor substituents thereof participate directly in SSRP/DNA lesion binding. Therefore, significant structural variation can be tolerated in the drug moieties located trans to the substitutionally labile chlorine atoms.

The invention thus provides a convenient in vitro screening procedure for assessing whether novel cisplatin analogs, or other chemotherapeutic candidates, form DNA lesions that are recognized and shielded from repair by SSRP family members. Novel genotoxic drug candidates can be synthesized individually or selected from a library of random products of combinatorial, e.g., synthesis as disclosed in Needels et al. (1993), 90 Proc. Natl. Acad. Sci. USA 10700 or Ohlmeyer et al. (1993), 90 Proc. Natl. Acad. Sci. USA 10922, the teachings of each of which are incorporated herein by reference. For example, a random combinatorial library of cisplatin-type drug candidates can be produced by allowing a cis-blocked platinum(II) preparation to react randomly with an amino acid preparation, such as a cocktail comprising some or all of the naturally occurring α-amino acids. New cisplatin-type drugs accordingly can be selected and further refined for their ability to form lesions that are bound with high affinity by a preferred SSRP, or that are bound by a panel of HMG domain SSRPs, tested singly or as a cocktail. Accordingly, the invention described herein encompasses new cisplatin-type chemotherapeutic drug candidates identified using the present screening assay. Further, the invention encompasses methods of making such new cisplatin-type chemotherapeutic drugs, comprising the steps of synthesizing a candidate cisplatin-type chemotherapeutic candidate and assessing the candidate for competence to produce SSRP-recognized genomic lesions. SSRP shielding of nucleic acid lesions can be assessed by any of the techniques disclosed herein. Thus, shielding can be assessed in vitro using a excinuclease assay generally according to Examples 3 and 4. Drug candidates which produce a high exinuclease shielding index in the present cell-free screening assay should be selected for further evaluation of antitumor efficacy, e.g., using transformed cell lines, primary cells in culture or animal models. Thus, the present invention offers the capacity to make more effective use traditional preclinical screening procedures.

The invention further provides new methods for sensitizing eukaryotic cells, e.g., transformed cells, to the cytotoxic effects of cisplatin-type genotoxins. These methods can be used to enhance the effectiveness of cisplatin-type chemotherapy by achieving a greater degree of cell killing than would be observed with current protocols at similar drug dosage levels. Further, these methods can be used to sensitize transformed cells that are refractory to killing by cisplatin-type genotoxins. In the present methods, nucleic acid encoding an SSRP or fragment thereof (e.g., an HMG domain) that binds to cisplatin-type DNA lesions, is contacted with the eukaryotic cells under conditions sufficient for uptake of foreign nucleic acids. SSRP encoding nucleic acids can be inserted into a vital vector, such as a retrovital vector, or packaged into liposomes, injected directly or transfected into eukaryotic cells using known techniques such as those reviewed in Mulligan (1993), 260 Science 926, the teachings of which are incorporated by reference herein. As mentioned previously, the eukaryotic cells can comprise cells of a unicellular or multicellular organism, and can comprise cells maintained in culture, cells withdrawn from a multicellular organism, or cells present in the tissues or organs of a multicellular organism. That is, the method can be practiced in vitro, ex vivo (using a sample, such as a biopsy, withdrawn from a multicellular organism such as a mammal, e.g., a human), or in vivo, by local or systemic administration to a multicellular organism.

For the treatment of malignancy in situ, retroviral vectors are preferred, as they will be selectively internalized by actively dividing cells, such as transformed cells. If desired, cells can be withdrawn from the individual, caused to internalize SSRP-encoding retroviral nucleic acid and reintroduced to the individual, preferably by local injection or infusion in the vicinity of transformed cells. The cells caused to internalize SSRP-encoding nucleic acid ex vivo accordingly provide a localized sustained release of SSRP-encoding nucleic acid that can be internalized and expressed by transformed cells in situ. See, e.g., Culver et al. (1992), 256 Science 1550, the teachings of which are incorporated by reference herein. Such methods can be used to achieve selective killing of neoplastic (transformed) cells throughout the body, e.g., cells of reproductive tract, cutaneous, mammary, or neurologic origin. Cells that are of reproductive tract origin can be more specifically, of ovarian, uterine, endometrial, cervical, vaginal, prostate, or testicular origin. Cells that are of mammary origin can be more specifically, of breast origin. Cells that are of cutaneous origin comprise basal cells, melanocytes, dendritic cells and cutaneous T lymphocytes. Cells that are of neurologic origin can be of central or peripheral nervous origin, and can be neurons, glia, Schwann cells and the like. Transformed cells of each of the foregoing tissue-specific origins can be caused to internalize SSRP encoding nucleic acids and express the encoded heterologous SSRP. Use of suitable expression control sequences will optionally cause overexpression of the heterologous SSRP, which is expected to significantly enhance susceptibility of the eukaryotic cells to cisplatin-type drug cytotoxicity, by ensuring an intracellular excess of SSRPs to shield cisplatin-type lesions from repair.

For in situ use to destroy transformed cells in the tissues of a multicellular organism (e.g., a mammal) the protocols for administering nucleic acid encoding SSRP will vary depending on the location of cells to be destroyed, replicative rate of the cells, level of repair proficiency of the cells, dose of genotoxic drug to be administered, route of delivery thereof, and pharmacokinetic profiles of clearance and tissue uptake of both the SSRP encoding nucleic acid and the genotoxic drug. Variables affecting the amounts needed thus include, but are not limited to, the nature (e.g., species or tissue type), quantity and accessibility (i.e., body compartment location) of eukaryotic cells to be destroyed, and the nature, genotoxicity, and affinity of the cisplatin-type genotoxin. Thus, as appropriate, SSRP encoding nucleic acid can be combined with a pharmaceutically acceptable carrier or excipient for formulation as a liquid, suspension, solid, salve, ointment or the like, suitable for oral, nasal, intravenous, intracerebral, intraspinal, intraperitoneal, topical, subdermal, intramuscular, or other routes of administration. SSRP encoding nucleic acid can be administered in a single dose (e.g., a bolus injection), a series of doses of equivalent, escalating, decreasing or intermittently varied quantity, or infused over a period of time (e.g., by intravenous drip or infusion), or by release from a slow-release delivery vehicle. The appropriate dose will of course be dictated by the precise circumstances under which the invention is practiced, but will generally be in the range of 0.01 ng to 10 g per kg body weight, preferably in the range of 1 ng to 0.1 g per kg, and more preferably in the range of 100 ng to 10 mg per kg.

Following uptake and expression intracellularly of the encoded SSRP, both of which can be monitored if preferred using standard techniques or routine modifications thereof, the cisplatin-type genotoxic agent is administered. Thereafter, the degree of eukaryotic cell killing achieved can be ascertained through standard, widely available techniques, such as visual or microscopic inspection, biochemical, chromogenic or immunologic methods for detecting products of eukaryotic cell lysis, and the like. Such techniques can be used to establish both the dose and time period effective to accomplish objectives of the present invention under particular circumstances. Once effective doses and time periods are established, it may be no longer necessary to monitor the progress of cell killing.

Practice of the invention will be still more fully understood from the following examples, which are presented herein for illustration only and should not be construed as limiting the invention in any way.

EXAMPLE 1

Removal of Defined Cisplatin Lesions from DNA by Human Exinuclease

Exinuclease Substrates with Defined Cisplatin Lesions.

Nucleic acid fragments (oligomers) bearing a 1,2-d(G^G) or a 1,3-d(GTG) cisplatin crosslink at a defined site were prepared essentially according to the method of Shi et al. (1987), 15 *Nucleic Acids Res.* 6843, by ligation of a mixture of a cisplatin-lesioned dodecamer with seven other oligonucleotides to produce 156 bp fragments. Prior to ligation, lesioned dodecamers were labeled with [$\gamma$-$^{32}$P]ATP such that the detectable radiolabel would be located at the 4th phosphodiester bond 5' to the 1,3-intrastrand d(GTG) lesion, or the 5th phosphodiester bond 5' to the 1,2-intrastrand d(G^G) lesion. Thus, the radiolabel would be included in the 27–29 nucleotide fragment spanning the cisplatin lesion that would be released by exinuclease. Full length (156 bp) exinuclease substrate oligomers were isolated on a 5% polyacrylamide/8 M urea denaturing gel and reannealed.

Sources of cell-free extracts (CFE) comprising exinuclease.

The HeLa S3 cell line was obtained from Lineberger Comprehensive Cancer Center (University of North Carolina School of Medicine), the human fibroblast XP-F cell line (XP2YO, GM08437A) from NIGMS Human Mutant Cell Repository (Coriell Institute, Camden, N.J.), and the XP-G rodent cell line (CHO-UV135, CRL1867) from the American Type Culture Collection Repository (Rockville, Md.).

Exinuclease Reaction.

The excision reaction buffer contained 40 mM Hepes, pH 7.9, 80 mM KCl, 8 mM $MgCl_2$, 2 mM ATP, 20 μM of each dNTP, 1 mM dithiothreitol, 0.3 mM EDTA, 6.8% (v/v) glycerol, and 200 μg/ml bovine serum albumin. The reaction mixture (50 μl) contained 100 μg of CFE (in cases of complementation, 50 μg of each of the XP CFE) and 30 pM DNA substrate (specific activity 7000 Ci/mmol), plus 250 ng pBR322 as carrier DNA. The excision reaction was carried out varying lengths of time at 30° C. Following proteinase K digestion, DNA exinuclease reaction products were extracted by phenol/chloroform and precipitated with ethanol. Equal amounts of DNA were loaded onto each lane.

Results.

Incubation of the defined, cisplatin-lesioned substrates with HeLa cell-free extract (CFE) (Manley et al. (1980), 77 *Proc. Natl. Acad. Sci, USA* 3855), resulted in the release of radiolabelled oligonucleotide patches comprising the cisplatin lesions. The excised patches were predominantly 27–29 nucleotides in length. The range of excision in 90 min ranged from 1–8% for the 1,2-d(G^G) crosslink and from 2.3–8% for the 1,3-d(GTG) crosslink in over 20 independent assays that were conducted. Batch to batch variability was observed both with respect to preparations of CFE and substrate. In only one experiment was the 1,2 adduct excised more efficiently.

In a comparison study, substrates were incubated with cell-free extracts from xeroderma pigmentosum complementation groups F and G or a mixture of the two (complementation), or with HeLa (H) cell-free extract. Incubation was allowed to proceed for 75 min., after which DNA reaction products were analyzed on 10% polyacrylamide denaturing gels. CFE from XP-F or XP-G cells did not contain significant exinuclease activity. Activity was, however, restored by mixing (complementation) of the two. The level of lesion repair achieved with F/G complementation was comparable to that observed for the HeLa extract. Slower migrating bands observed near the top of the gel were presumed to arise from non-specific nuclease activity, and the fastest migrating species (<25 nucleotides) at the bottom of the gel were presumed to result from exonucleolytic degradation of the primary 27–29 nucleotide excision products. Svoboda et al. (1993), 268 *J. Biol. Chem.* 1931.

EXAMPLE 2

Timecourse Study of d(GTG) and d(G^G) Lesion Removal by Human Exinuclease

The radiolabeled substrates bearing specific 1,2- and 1,3-intrastrand cisplatin lesions and the HeLa cell-free extract described above in Example 1 were used.

Exinuclease timecourse reaction.

Reaction mixtures contained 21 pM DNA substrate and 50 μg CFE in 25 μl reaction buffer for each time point. The reaction was carried out at 30° C. At 15, 30, 60 and 90 min., reactions were stopped by adding SDS to 1% and proteinase K to 0.4 mg/ml in the reaction mixtures. DNA reaction products were extracted from the mixtures by phenol/chloroform, and subsequently resolved on 10% polyacrylamide denaturing gels. The level of excision was quantified by an Ambis scanner, and results were plotted as the averages of two independent timecourses. Autoradiographs were also obtained for visual display of raw data.

Results.

FIG. 4 is a kinetic plot of the results of duplicate timecourse studies. Both the initial rate and plateau level of excision of the 1,3-intrastrand crosslink exceeded the corresponding values for excision of the 1,2-intrastrand crosslink. The 30 min. timepoint was selected for studies of the affects of HMG-box proteins on the initial rate of excision of cisplatin lesions, as this timepoint falls near the center of the linear portion of the kinetic plot.

EXAMPLE 3

HMG1 Inhibition of Exinuclease Repair

Source of HMG1 Protein.

Recombinant HMG1 protein was purified from an E. coli overproducing strain as described in Pil and Lippard (1992), 256 *Science* 234, and stored in 50 mM Tris-HCl, pH 7.3, 50 mM NaCl, and 5 mM β-mercaptoethanol.

The radiolabeled substrates bearing specific 1,2- and 1,3-intrastrand cisplatin lesions and the HeLa cell-free extract described above in Example 1 were used.

Gel Mobility Shift Assay.

The 25 μl reaction mixtures contained 30 pM substrate and 0, 1, 2, 4 or 8 μM HMG1. Mixtures were incubated at 30° C. for 10 min. Samples (1.5 μl) of the mixtures were withdrawn and adjusted to 15% (v/v) glycerol, and electrophoretically resolved on a 5% native polyacrylamide gel. Results were visualized by autoradiography.

Exinuclease Reaction in the Presence of HMG1.

Following withdrawal of the above samples for gel mobility shift analysis, 50 μg of HeLa CFE was added to each of the reaction mixtures and incubation was continued for 30 min at 30° C. as described in Example 1. Reactions were stopped and DNA reaction products were retrieved and analyzed as described in Example 2.

Results.

FIG. 5 is a concentration plot showing the affect of HMG1 on the excision of cisplatin intrastrand lesions. The data points are averages of 2-3 experiments. The excision levels in the absence of inhibitor were 2.1, 1.7, 1.5 percent of the substrate for the 1,2-dinucleotide crosslink, and 2.6, 2.6, and 2.5 for the 1,3-dinucleotide crosslink in the three experiments. The results establish that HMG1 specifically inhibits the excision of 1,2-D(GpG) cisplatin lesions, while slightly stimulating the excision of 1,3-d(GpTpG) lesions. The latter result might be attributable to HMG1 bending of the DNA substrate in a manner favorable for exinuclease activity.

EXAMPLE 4 h-mtTFA Inhibition of Exinuclease Repair

An exinuclease inhibition study was carried out generally as described in Example 3, using 0, 0.5 or 1.0 μM concentrations of HMG1 or h-mtTFA in parallel incubations. Results are presented below in TABLE 1. Both HMG-box proteins showed specificity for the 1,2-dinucleotide adduct of cisplatin, with h-mtTFA producing a more pronounced inhibitory effect.

TABLE 1

Comparison of the Effects of HMG1 and h-mtTFA on Repair of Site-Specific Cisplatin Adducts*

| Adduct | HMG1 percent inhibition | | | h-mtTFA percent inhibition | | |
|---|---|---|---|---|---|---|
| | 0 μM | 0.5 μM | 1 μM | 0 μM | 0.5 μM | 1 μM |
| 1,2-GG | 0 | 20 | 40 | 0 | 95 | 100 |
| 1,3-GTG | 0 | 0 | 0 | 0 | 40 | 75 |

*Average inhibition of repair in two experiments.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

---

What is claimed is:

1. A method for predicting cytotoxicity of an agent that binds to DNA to form a covalent 1,2-intrastrand d(ApG) or d(GpG) dinucleotide adduct, comprising the steps of:

(a) providing a sample of double-stranded DNA bearing a lesion formed by the binding of said agent to DNA;

(b) contacting said sample with a DNA structure-specific recognition protein having at least one HMG domain and being large enough to sterically obscure at least 5 base pairs of DNA adjacent to said lesion, under conditions such that a lesioned DNA/protein complex forms; and (c) detecting said complex, wherein formation of said complex indicates that said agent will be cytotoxic.

2. A method of identifying a cytotoxic agent that binds to DNA to form a genomic lesion comprising a covalent 1,2-intrastrand d(ApG) or d(GpG) dinucleotide adduct, comprising the steps of:

(a) contacting a sample of DNA with a candidate cytotoxic agent;

(b) incubating said DNA with said candidate under conditions sufficient for binding of cytotoxic agents to DNA;

(c) separating DNA bearing said lesion formed by the binding thereto of said cytotoxic agent from unlesioned DNA and unbound candidate;

(d) contacting DNA bearing said lesion with a DNA structure-specific recognition protein having at least one HMG domain and being large enough to sterically obscure at least 5 base pairs of DNA adjacent to said lesion, under conditions such that a lesioned DNA/protein complex forms; and (e) detecting said complex, wherein formation of said complex indicates that said agent will be cytotoxic.

3. A method of claim 1 or 2 wherein said complex is detected by nitrocellulose filter retention assay, electrophoretic mobility shift assay or Southwestern blotting.

4. A method of claim 1 or 2 wherein, in the absence of said protein, said lesion is excisable and wherein formation of said complex shields said lesion from excision in an excinuclease protection assay.

5. A method of claim 4 wherein said excinuclease protection assay comprises the steps of:

(i) contacting said complex with excinuclease;

(ii) incubating said complex with excinuclease under conditions sufficient for the removal of lesions from DNA; and (iii) detecting whether said lesion has been removed from DNA, wherein failure to remove said lesion indicates that said agent will be cytotoxic due to the formation of persistent genomic lesions in eukaryotic cellular DNA.

6. A method of claim 1 or 2 wherein said agent is a metal coordination compound.

7. A method of claim 6 wherein agent is a platinum compound.

8. A method of claim 7 wherein said agent is a platinum (II) or platinum(IV) compound comprising a platinum atom linked to a pair of cis configured substitutionally labile moieties and a pair of cis configured electron donor moieties.

9. A method of claim 1 wherein said structure-specific recognition protein is encoded by nucleic acid that hybridizes specifically to a nucleic acid probe encoding amino acid residues 539–614 of SEQ ID No. 2.

10. A method of claim 9 wherein said structure-specific recognition protein is of human, rodent, Xenopus, Drosophila or yeast origin.

11. A method of claim 9 wherein said structure-specific recognition protein comprises at least one domain having an amino acid sequence selected from residues 539–614 of SEQ ID No. 2, residues 547–620 of SEQ ID No. 6, and amino acid sequence variants thereof that retain HMG domain DNA binding properties.

12. A method of claim 11 wherein said structure-specific recognition protein has an amino acid sequence selected from SEQ ID No. 2, SEQ ID No. 6, and amino acid sequence variants thereof that retain HMG domain DNA binding properties.

13. A method of claim 1 wherein said structure-specific recognition protein is selected from the group consisting of HMG1, HMG2, UBF, LEF-1, SRY, mtTFA, ABF2, IXR1 and SSRP.

* * * * *

UNITED STATES PATENT AND TRADEMARK OFFICE
CERTIFICATE OF CORRECTION

PATENT NO. : 5,705,334
DATED : January 6, 1998
INVENTOR(S) : Lippard et al.

It is certified that error appears in the above-identified patent and that said Letters Patent is hereby corrected as shown below:

In Claim 1, at Column 55, line 59, delete "beating" and insert -- bearing --.

In Claim 2, at Column 56, line 65, delete "beating" and insert -- bearing --.

Signed and Sealed this

Twenty-third Day of June, 1998

*Attest:*

BRUCE LEHMAN

*Attesting Officer*   *Commissioner of Patents and Trademarks*